United States Patent
Nan et al.

(10) Patent No.: US 8,653,115 B2
(45) Date of Patent: *Feb. 18, 2014

(54) HETEROCYCLIC NON-NUCLEOSIDE COMPOUNDS, THEIR PREPARATION, PHARMACEUTICAL COMPOSITION AND THEIR USE AS ANTIVIRAL AGENTS

(75) Inventors: Fajun Nan, Shanghai (CN); Jianping Zuo, Shanghai (CN); Haijun Chen, Shanghai (CN); Guifeng Wang, Shanghai (CN); Min Gu, Shanghai (CN); Fenghua Zhu, Shanghai (CN); Wei Tang, Shanghai (CN)

(73) Assignee: Shanghai Institute of Materia Medica, Chinese Academy of Sciences, Shanghai (CN)

( * ) Notice: Subject to any disclaimer, the term of this patent is extended or adjusted under 35 U.S.C. 154(b) by 770 days.

This patent is subject to a terminal disclaimer.

(21) Appl. No.: 12/304,598

(22) PCT Filed: Jun. 13, 2007

(86) PCT No.: PCT/CN2007/001861
§ 371 (c)(1),
(2), (4) Date: Sep. 30, 2009

(87) PCT Pub. No.: WO2007/147336
PCT Pub. Date: Dec. 27, 2007

(65) Prior Publication Data
US 2010/0056569 A1    Mar. 4, 2010

(30) Foreign Application Priority Data
Jun. 13, 2006 (CN) .......................... 2006 1 0027724

(51) Int. Cl.
*A61K 31/426* (2006.01)
*C07D 277/24* (2006.01)

(52) U.S. Cl.
USPC ........... 514/365; 514/369; 548/183; 548/188; 548/200

(58) Field of Classification Search
USPC .................. 548/183, 188, 200; 514/365, 369
See application file for complete search history.

(56) References Cited

U.S. PATENT DOCUMENTS

| | | |
|---|---|---|
| 4,499,097 A | 2/1985 | Tomcufcik et al. |
| 4,732,895 A | 3/1988 | Hofmann et al. |
| 4,743,586 A | 5/1988 | Chan |
| 5,614,520 A | 3/1997 | Kondo et al. |
| 7,741,348 B2 * | 6/2010 | Nan et al. ....................... 514/365 |
| 2005/0187218 A1 | 8/2005 | Marinier et al. |

FOREIGN PATENT DOCUMENTS

| | | | |
|---|---|---|---|
| EP | 0097323 A2 | | 1/1984 |
| WO | 2004058174 A2 | | 7/2004 |
| WO | 2005082885 A1 | | 9/2005 |
| WO | 2006097030 | * | 9/2006 |
| WO | 2006097030 A1 | | 9/2006 |

OTHER PUBLICATIONS

Joshua C. Yoburn et al., "Chemoselective Arylamidine Cyclizations: Mild Formation of 2-Arylimidazole-4- carboxylic Acids", Organic Letters, 2005, pp. 3801-3803, vol. 7, No. 17, American Chemical Society Published on Web Jul. 23, 2005.

Caroline M. R. Low et al., "Scaffold Hopping with Molecular Field Points: Identification of a Cholecystokinin-2 (CCK2) Receptor Pharmacophore and Its Use in the Design of a Prototypical Series of Pyrrole-and Imidazole-Based CCK2 Antagonists", J. Med. Chem., 2005, pp. 6790-6802, vol. 48, American Chemical Society Published on Web Oct. 11, 2005.

Marion Giraud et al., "Synthesis and Photochromism of Two New 1,2-bis(thiazolyl) Perfluorocyclopentenes with Chelating sites", New J. Chem., 2005, pp. 439-446, vol. 29.

Jon L. Collins et al., "N-(2-Benzoylphenyl)-L-tyrosine PPARγ Agonists. 2. Structure-Activity Relationship and Optimization of the Phenyl Alkyl Ether Moiety", J. Med. Chem., 1998, pp. 5037-5054, vol. 41, American Chemical Society Published on Web Nov. 6, 1998.

* cited by examiner

*Primary Examiner* — Patricia L Morris
(74) *Attorney, Agent, or Firm* — Baker & Hostetler LLP

(57) ABSTRACT

The invention relates a kind of antiviral agents, more concretely, relates to a kind of heterocyclic non-nucleoside compounds with the following structures, their preparation and pharmaceutical compositions including the compounds. The said compounds can be used as antiviral agents and as medicaments for treating diseases such as hepatitis B, influenza, herpes, HIV and so on.

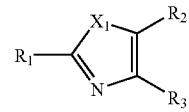

5 Claims, 1 Drawing Sheet

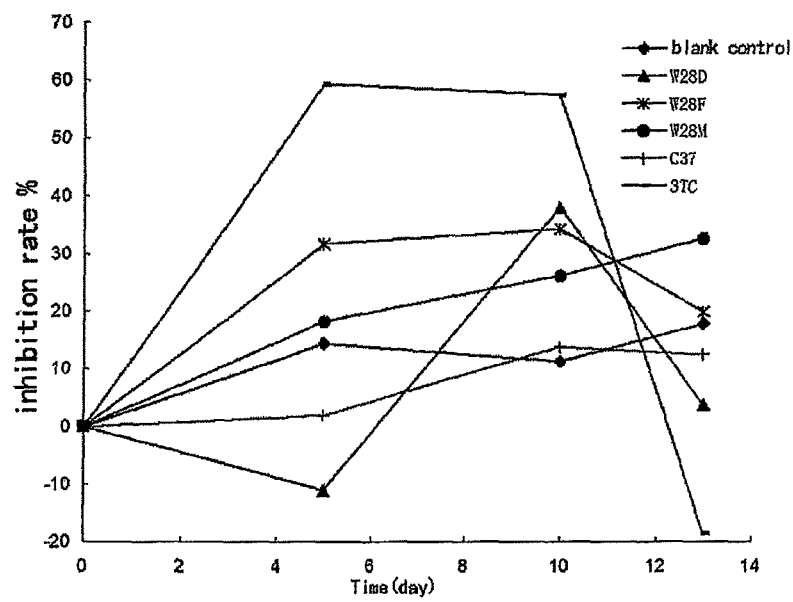

HETEROCYCLIC NON-NUCLEOSIDE COMPOUNDS, THEIR PREPARATION, PHARMACEUTICAL COMPOSITION AND THEIR USE AS ANTIVIRAL AGENTS

CROSS-REFERENCED TO RELATED APPLICATIONS

This is a national stage of International Application No. PCT/CN2007/001861, filed on Jun. 13, 2007, which claims priority of Chinese Patent Application No. 200610027724.0, filed Jun. 13, 2006, the disclosure of each application is hereby incorporated by reference in their entirety.

TECHNICAL FIELD

The present invention relates to a kind of antiviral inhibitors, particularly to a kind of heterocyclic non-nucleoside compounds, their preparing methods, and pharmaceutical compositions including the same. The said compounds can be used as antiviral inhibitors and as medicaments for treating diseases such as hepatitis B, influenza, herpes, AIDS and so on.

BACKGROUND ART

Human pathogenic viruses are a kind of nucleic acid particles with very simple structure. Most of them lack enzymatic system, and have to depend on the host cells to replicate their nucleic acids and proteins and then assemble into virus particles so as to realize the multiplication of the viruses. Viral infection can cause various diseases and harm the health and lives of human severely. With the undercount, about 60% epidemical diseases are caused by viral infection. Up to now, more than 3000 kinds of viruses have been found all over the world, and new viruses are being continuously found. At the World Virology Convention held in Paris in August 2002, the $7^{th}$ report of International Committee on the Taxonomy of Viruses embodies more than 3600 kinds of viruses, in which more than 1200 kinds of viruses are pathogenic to human and can be divided into 29 families, 7 subfamilies and 53 genera. At present, the viruses with high morbidity and great harmfulness mainly include influenza virus, hepatitis B virus, AIDS virus, cytomegalovirus and herpes virus, etc.

Now there still lacks of drugs with high specificity in the treatment of viral diseases, and also the commonly used drugs in clinical therapy mainly are divided into the following types: the antiviral drugs for inhibiting viral replication; the immunomodulators for enhancing the body's immune function; the antitussive, anodyne, antipyretic and antiphlogistic and the like against clinical symptoms; the anti-infection drugs for preventing secondary infection; the vaccines for preventing viral infection and the disinfectants for blocking the transmission of viruses, etc.

The study of new drugs for treating viral diseases abroad focuses on the antiviral drugs. At present, the anti-influenza virus drugs include the adamantine amine drugs, the neuraminidase inhibitors of influenza virus, the receptor blocking agent of influenza virus and the antisense oligonucleotide against influenza virus etc. And the ones used in clinical therapy mainly are the adamantanamine drugs and the neuraminidase inhibitors. However, the hepatitis virus infection is a well-known difficulty in therapeutics so far. More than 80% of the acute infection of the hepatitis B virus (HBV), hepatitis C virus (HCV) and hepatitis D virus (HDV) will convert into chronic infection, in which 20% persistent infection may develop to hepatic cirrhosis, and 1% to 5% will change to hepatoma carcinoma. The world health organization has classified hepatitis as the 9th cause of death. China is a region with high incidence of viral hepatitis, and the carriers of hepatitis B virus are more than 120 million. It is estimated that the direct economic loss resulted from viral hepatitis is 30 billion to 50 billion RMB. Therefore, it is a main task for the medical and pharmaceutical domestic and abroad scientists to explore and develop antiviral drugs. The vidarabine, vidarabine phosphate, acyclovir, zidovudine studied in 1980's are not used to treat hepatitis B now abroad due to their poor therapeutic effect and strong toxic adverse effect. In recent years, many large-scale enterprises developed various nucleoside drugs having obvious inhibitory effect to HBV, such as lamivudine, famciclovir, lobucavir, adefovir dipivoxiil, FTC (dideoxyfluorinethiocytosine), FMAU (fluoromethylarabinosyluracil), FDDC (fluoro-dideocytosine), BMS 200475 (epoxyhydroxylcarbodeoxy guanosine), by using the established hepatoma carcinoma cell lines, hepatitis virus transfected cell lines or transgenic cell lines, and transgenic mouse hepatitis animal model to screen the drugs against hepatitis B virus and hepatitis C virus. The researchers abroad carried out the preclinical research on more than 30 kinds of drugs in 1998-2002. And recently there are 21 drugs entering stage II-III clinical trial, and among them, the trial medicaments for anti-hepatitis B virus are mostly derived from the HIV revertase inhibitor and herpes virus DNA polymerase inhibitor, in which enticavir has been authorized to be commercially available in 2005. Most of the trail medicaments for anti-hepatitis C virus are derived from broad-spectrum antiviral drugs or RNA virus inhibitors and the immunomodulators having antiviral activity.

At present, most of the authorized antivirus drugs are nucleoside compounds. During the clinical uses, they have the following disadvantages: 1) cytotoxicity; 2) occurrence of drug resistant viruses variants induced by long-term medication and the requirement of the other drugs having different structure to antagonize these variants. Therefore, developing non-nucleoside antiviral drugs becomes an arresting aspect.

DISCLOSURE OF THE INVENTION

An object of the present invention is to design and synthesize a kind of new heterocyclic non-nucleoside compounds as antiviral inhibitors so as to pave the way for finding precursor compounds or antiviral drugs for the research of antiviral drugs.

Another object of the present invention is to provide methods for preparing heterocyclic non-nucleoside compounds of the present invention.

Still another object of the present invention is to provide a pharmaceutical composition containing the heterocyclic non-nucleoside compounds of the present invention as active components.

Further another object of the present invention is to provide uses of the heterocyclic non-nucleoside compounds of the present invention in preparing medicaments for treating viral diseases.

The heterocyclic non-nucleoside compounds provided by the present invention have a structure represented by the following formula:

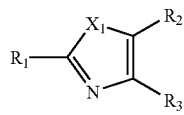

wherein, $X_1$ is $NR_4$, O or S;

$R_1$ is pyridyl, substituted pyridyl, phenyl, substituted phenyl, 5-membered heterocyclic group, substituted 5-membered heterocyclic group or fused heterocyclic group, wherein the 5-membered heterocyclic group is one containing one or two hetero atoms selected from the group consisting of N, O and S, and the fused heterocyclic group is quinolyl or indolyl;

Each $R_2$ and $R_3$ is one independently selected from the group consisting of H; halogen atom; nitro group; $C_1$-$C_{25}$ alkyl; $C_1$-$C_{25}$ alkyl substituted by halogen atom, $C_1$-$C_{25}$ alkyl, $C_3$-$C_{25}$ cycloalkyl, $C_1$-$C_{25}$ alkoxyl, $C_3$-$C_{25}$ cycloalkoxyl, $C_2$-$C_{25}$ alkenyl, $C_3$-$C_{25}$ cycloalkenyl, nitro group, amino group, $C_1$-$C_{25}$ alkylamino group, $C_3$-$C_{25}$ cycloalkylamino group, $C_1$-$C_{25}$ alkyl amide group, hydroxyl group, acyloxy or $C_1$-$C_4$ alkoxycarbonyl; hydroxyl group; amino group; $C_1$-$C_{25}$ alkylamino group; $C_3$-$C_{25}$ cycloalkylamino group; $C_3$-$C_9$ cycloalkyl; $C_3$-$C_9$ cycloalkyl substituted by halogen atom, $C_1$-$C_{25}$ alkyl, $C_3$-$C_{25}$ cycloalkyl; $C_1$-$C_{25}$ alkoxyl, $C_3$-$C_{25}$ cycloalkoxyl, $C_2$-$C_{25}$ alkenyl, $C_3$-$C_{25}$ cycloalkenyl, nitro group, amino group, $C_1$-$C_{25}$ alkylamino group, $C_3$-$C_{25}$ cycloalkylamino group, $C_1$-$C_{25}$ alkyl amide group, hydroxyl or acyloxy; aryl; aryl substituted by halogen atom, $C_1$-$C_{25}$ alkyl, $C_3$-$C_{25}$ cycloalkyl, $C_1$-$C_{25}$ alkoxyl, $C_3$-$C_{25}$ cycloalkoxyl, $C_2$-$C_{25}$ alkenyl, $C_3$-$C_{25}$ cycloalkenyl, nitro group, amino group, $C_1$-$C_{25}$ alkylamino group, $C_3$-$C_{25}$ cycloalkylamino group, $C_1$-$C_{25}$ alkyl amide group, hydroxyl or acyloxy; benzyl; benzyl substituted by halogen atom, $C_1$-$C_{25}$ alkyl, $C_3$-$C_{25}$ cycloalkyl, $C_1$-$C_{25}$ alkoxyl, $C_3$-$C_{25}$ cycloalkoxyl, $C_2$-$C_{25}$ alkenyl, $C_3$-$C_{25}$ cycloalkenyl, nitro group, amino group, $C_1$-$C_{25}$ alkylamino group, $C_3$-$C_{25}$ cycloalkylamino group, $C_1$-$C_{25}$ alkyl amide group, hydroxyl or acyloxy; $C_2$-$C_{25}$ alkenyl; $C_2$-$C_{25}$ alkenyl substituted by halogen atom, $C_1$-$C_{25}$ alkyl, $C_3$-$C_{25}$ cycloalkyl, $C_1$-$C_{25}$ alkoxyl, $C_3$-$C_{25}$ cycloalkoxyl, nitro group, amino group, $C_1$-$C_{25}$ alkylamino group, $C_3$-$C_{25}$ cycloalkylamino group, $C_1$-$C_{25}$ alkyl amide group, hydroxyl, acyloxy or $C_1$-$C_4$ alkoxycarbonyl; $C_3$-$C_{25}$ cycloalkenyl; $C_3$-$C_{25}$ cycloalkenyl substituted by halogen atom, $C_1$-$C_{25}$ alkyl, $C_3$-$C_{25}$ cycloalkyl, $C_1$-$C_{25}$ alkoxyl, $C_3$-$C_{25}$ cycloalkoxyl, nitro group, amino group, $C_1$-$C_{25}$ alkylamino group, $C_3$-$C_{25}$ cycloalkylamino group, $C_1$-$C_{25}$ alkyl amide group, hydroxyl or acyloxy;

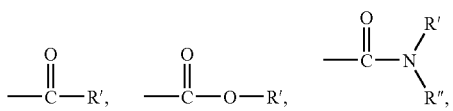

wherein each R' and R" independently is hydrogen atom, $C_1$-$C_{25}$ alkyl, halogenated $C_1$-$C_{10}$ alkyl, aryl, benzyl, substituted benzyl, $C_1$-$C_6$ hydroxyalkyl, substituted or unsubstituted heterocyclic methylene, wherein the substituents on benzyl may be halogen, $C_1$-$C_{10}$ alkyl, $C_1$-$C_{10}$ alkoxyl, $C_1$-$C_{10}$ alkylamino group, nitrile group, carboxyl or $C_1$-$C_{10}$ alkoxycarbonyl; and ureido group or ureylene;

$R_4$ is H, aryl, substituted aryl, benzyl, $C_1$-$C_{13}$ alkyl, substituted $C_1$-$C_{13}$ alkyl, $C_2$-$C_6$ alkenyl or $C_3$-$C_6$ cycloalkyl, wherein the substituents on the said aryl or $C_1$-$C_{13}$ alkyl may be halogen atom, alkoxyl, amino group, alkylamino group or hydroxyl.

In one preferable embodiment of the present invention, the said $X_1$ is $NR_4$, $R_4$ is hydrogen atom or $C_1$-$C_4$ alkyl;

$R_1$ preferably is pyridyl, substituted pyridyl, thiazolyl, substituted thiazolyl, quinolyl or indolyl, wherein the substituent(s) of the substituted pyridyl and substituted thiazolyl is one or two selected from the group of hydroxyl, halogen atom, nitro group, $C_1$-$C_4$ alkyl, $C_1$-$C_4$ alkoxyl, phenyl, benzyl and $C_1$-$C_4$ alkoxycarbonylamino group; and $R_1$ further preferably is 2-pyridyl, 2-thiazolyl, 2-quinolyl or 2-indolyl;

$R_2$ preferably is linear or branched $C_1$-$C_8$ alkyl or $C_3$-$C_8$ cycloalkyl, more preferably linear or branched $C_1$-$C_6$ alkyl or $C_3$-$C_6$ cycloalkyl, such as methyl, ethyl, propyl, butyl, pentyl, hexyl, cyclopropyl, cyclobutyl, cyclopentyl or cyclohexyl, most preferably isobutyl or cyclohexyl;

$R_3$ is

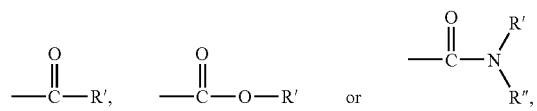

wherein each R' and R" independently is hydrogen atom, $C_1$-$C_{25}$ alkyl, halogenated $C_1$-$C_{10}$ alkyl, aryl, benzyl, halogenated benzyl, benzyl substituted by $C_1$-$C_{10}$ alkyl, benzyl substituted by $C_1$-$C_{10}$ alkoxyl, benzyl substituted by $C_1$-$C_{10}$ alkylamino group, benzyl substituted by nitrile group, benzyl substituted by carboxyl, benzyl substituted by $C_1$-$C_{10}$ alkoxycarbonyl, substituted or unsubstituted heterocyclomethylene; more preferably $R_3$ is

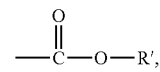

wherein R' is $C_1$-$C_6$ linear or branched alkyl, and preferably $C_1$-$C_4$ linear or branched alkyl, most preferably ethyl;

In this embodiment, the representative specific compound of the present invention is one of the following compounds:

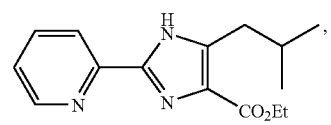
(C273)

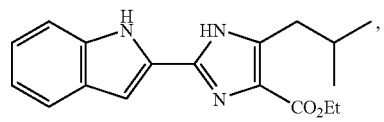
(C311-2)

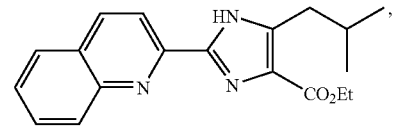
(C323)

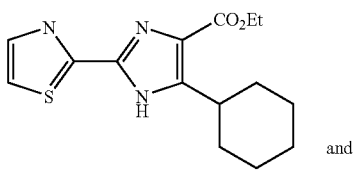 (C305-2)

and

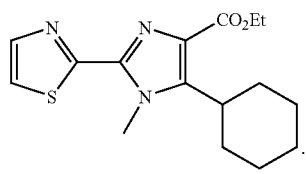 (C319-6)

In another preferable embodiment of the present invention, $X_1$ is O;

$R_1$ preferably is pyridyl, substituted pyridyl, quinolyl or indolyl, wherein the said substituted pyridyl is pyridyl substituted by one or two substituents selected from hydroxyl, halogen atom, nitro group, $C_1$-$C_4$ alkyl, $C_1$-$C_4$ alkoxyl, phenyl, benzyl and $C_1$-$C_4$ alkoxycarbonylamino group; and $R_1$ further preferably is 2-pyridyl, 2-quinolyl or 2-indolyl;

$R_2$ preferably is linear or branched $C_1$-$C_8$ alkyl or $C_3$-$C_8$ cycloalkyl, more preferably linear or branched $C_1$-$C_6$ alkyl or $C_3$-$C_6$ cycloalkyl, such as methyl, ethyl, propyl, butyl, pentyl, hexyl, cyclopropyl, cyclobutyl, cyclopentyl or cyclohexyl, most preferably isobutyl;

$R_3$ is

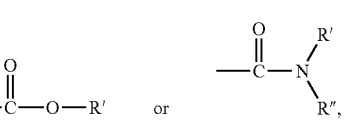

wherein each R' and R" independently is hydrogen atom, $C_1$-$C_{25}$ alkyl, halogenated $C_1$-$C_{10}$ alkyl, aryl, benzyl, halogenated benzyl, benzyl substituted by $C_1$-$C_{10}$ alkyl, benzyl substituted by $C_1$-$C_{10}$ alkoxyl, benzyl substituted by $C_1$-$C_{10}$ alkylamino group, benzyl substituted by nitrile group, benzyl substituted by carboxyl, benzyl substituted by $C_1$-$C_{10}$ alkoxycarbonyl, substituted or unsubstituted heterocyclomethylene; more preferably $R_3$ is

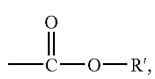

wherein R' is linear or branched $C_1$-$C_6$ alkyl, and preferably linear or branched $C_1$-$C_4$ alkyl, most preferably ethyl;

In this embodiment, the representative specific compound of the present invention is one of the following compounds:

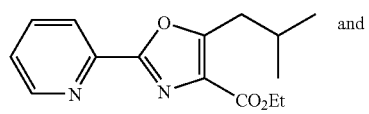 (C274)

and

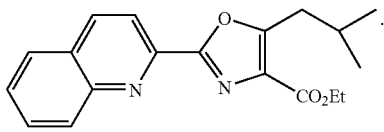 (C324-4)

In still another preferable embodiment of the present invention, $X_1$ is S;

$R_1$ preferably is pyridyl, substituted pyridyl, phenyl, substituted phenyl, thiazolyl, substituted thiazolyl, quinolyl or indolyl; wherein the said substituted pyridyl, substituted phenyl and substituted thiazolyl are respectively pyridyl, phenyl and thiazolyl each of which are substituted by one or two substituents selected from hydroxy, halogen atom, nitro group, $C_1$-$C_4$ alkyl, $C_1$-$C_4$ alkoxyl, phenyl, benzyl and $C_1$-$C_4$ alkoxycarbonylamino group; and $R_1$ further preferably is pyridyl; pyridyl substituted by hydroxy; phenyl; phenyl substituted by one or two substituents selected from hydroxyl, halogen atom, nitro group, $C_1$-$C_4$ alkyl, $C_1$-$C_4$ alkoxyl, phenyl and $C_1$-$C_4$ alkoxycarbonylamino group; 2-thiazolyl; 2-thiazolyl substituted by halogen atom, phenyl or $C_1$-$C_4$ alkyl; 2-quinolyl or 2-indolyl;

Most preferably, the said heterocyclic non-nucleoside compounds have a structure represented by the following formula I:

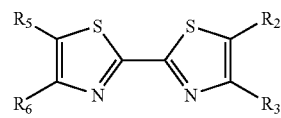 I

Wherein each $R_5$ and $R_6$ independently is hydrogen atom, halogen atom, linear or branched $C_1$-$C_4$ alkyl or phenyl;

$R_2$ preferably is linear or branched $C_1$-$C_8$ alkyl, $C_3$-$C_8$ cycloalkyl or benzyl, more preferably linear or branched $C_1$-$C_6$ alkyl, $C_3$-$C_6$ cycloalkyl or benzyl, such as methyl, ethyl, propyl, butyl, pentyl, hexyl, cyclopropyl, cyclobutyl, cyclopentyl or cyclohexyl, most preferably isobutyl, n-butyl or benzyl;

$R_3$ is one selected from hydrogen atom; $C_1$-$C_6$ hydroxyalkyl; $C_1$-$C_4$ alkyl substituted by $C_1$-$C_4$ alkoxycarbonyl; $C_2$-$C_4$ alkenyl substituted by $C_1$-$C_4$ alkoxycarbonyl;

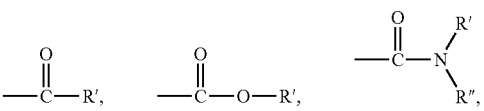

wherein each R' and R" independently is hydrogen atom, $C_1$-$C_{25}$ alkyl, halogenated $C_1$-$C_{10}$ alkyl, aryl, benzyl, halogenated benzyl, benzyl substituted by $C_1$-$C_{10}$ alkyl, benzyl substituted by $C_1$-$C_{10}$ alkoxy, benzyl substituted by $C_1$-$C_{10}$ alkylamino group, benzyl substituted by nitrile group, benzyl substituted by carboxyl, benzyl substituted by $C_1$-$C_{10}$ alkoxycarbonyl, substituted or unsubstituted heterocyclomethylene.

Further preferably, $R_3$ is one group selected from hydrogen atom; $C_1$-$C_4$ hydroxyalkyl; ethoxycarbonylethylene; ethoxycarbonylvinyl;

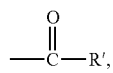

wherein R' is linear or branched $C_1$-$C_4$ alkyl;

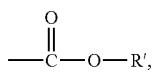

wherein R' is hydrogen atom or linear or branched $C_1$-$C_4$ alkyl;

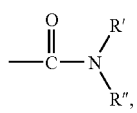

wherein each R' and R" independently is hydrogen atom, linear or branched $C_1$-$C_4$ alkyl, phenyl, benzyl, fluorobenzyl or 4-[2-(2-thiazolyl)-5-isobutyl-thiazolyl]methylene;

In this embodiment, the representative specific compound of the present invention is one of the following compounds:

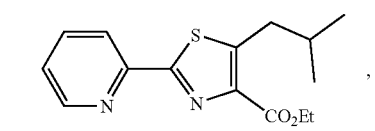
(C290)

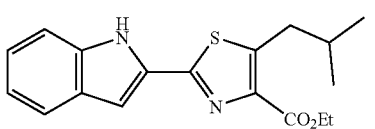
(C328-2)

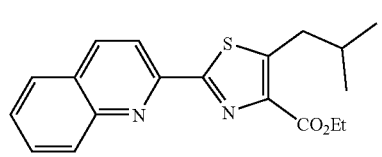
(C340)

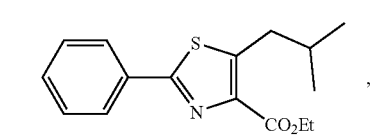
(C289)

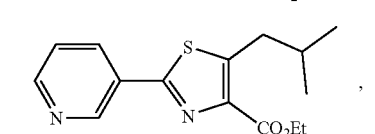
(C290-2)

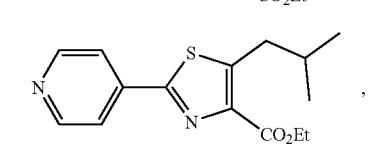
(C290-3)

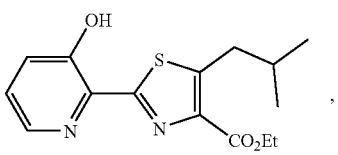
(C306-3)

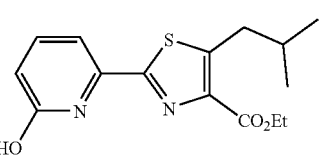
(C306-2)

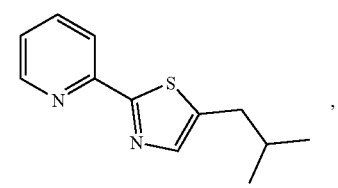
(C218)

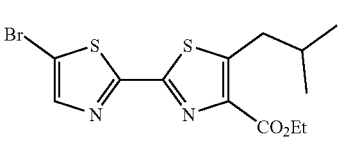
(C375)

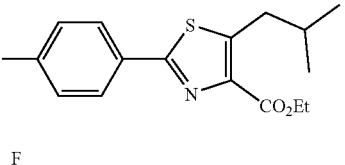
(C307-2)

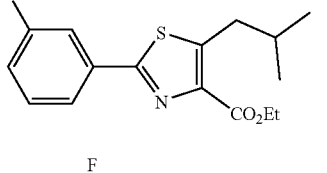
(C307-3)

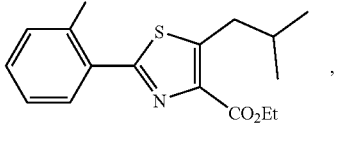
(C307-4)

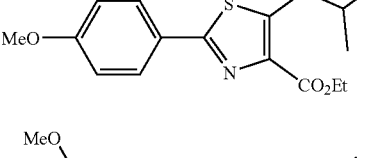
(C319-3)

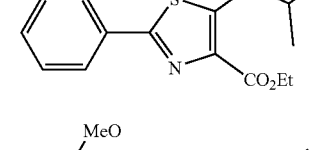
(C319-4)

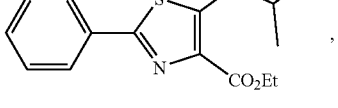
(C319-5)

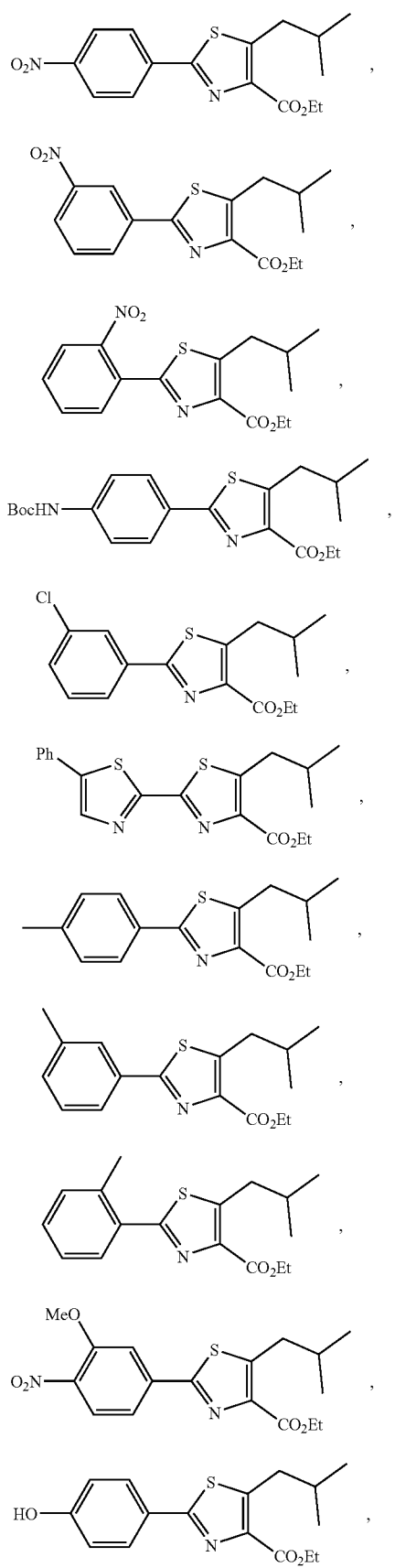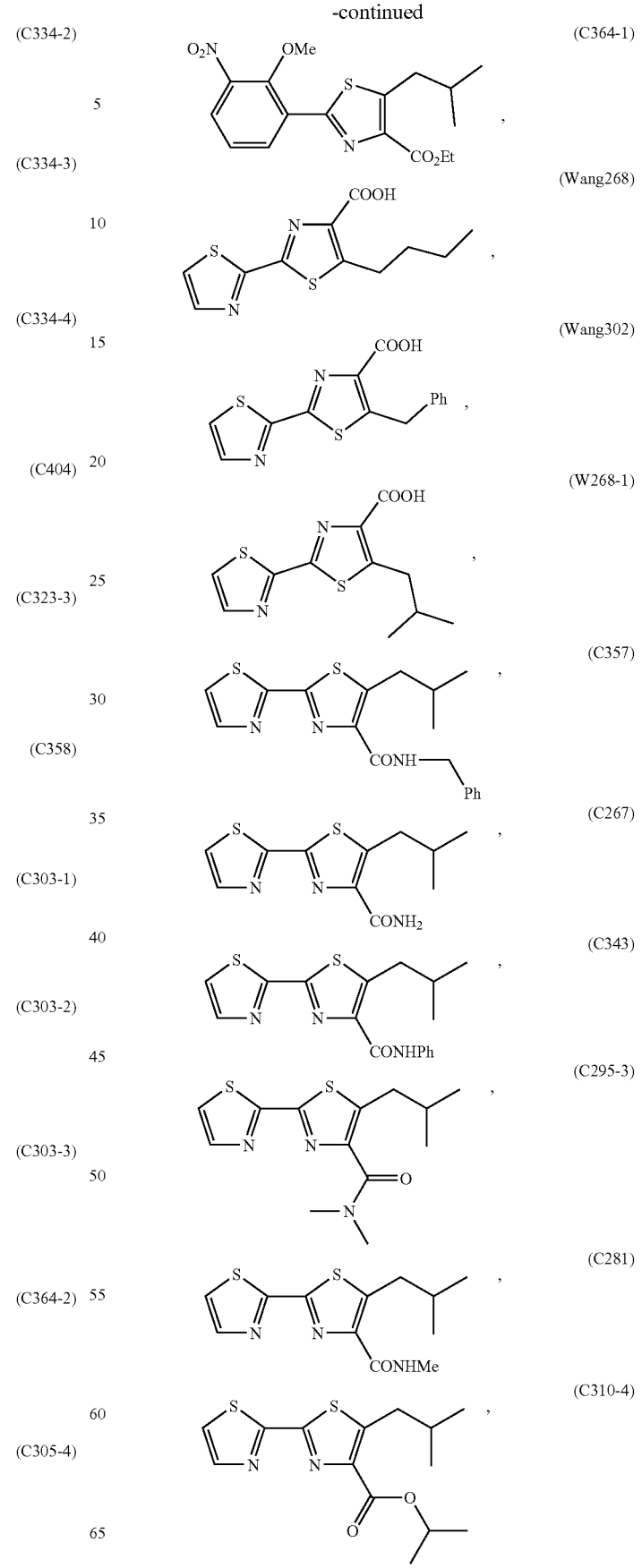

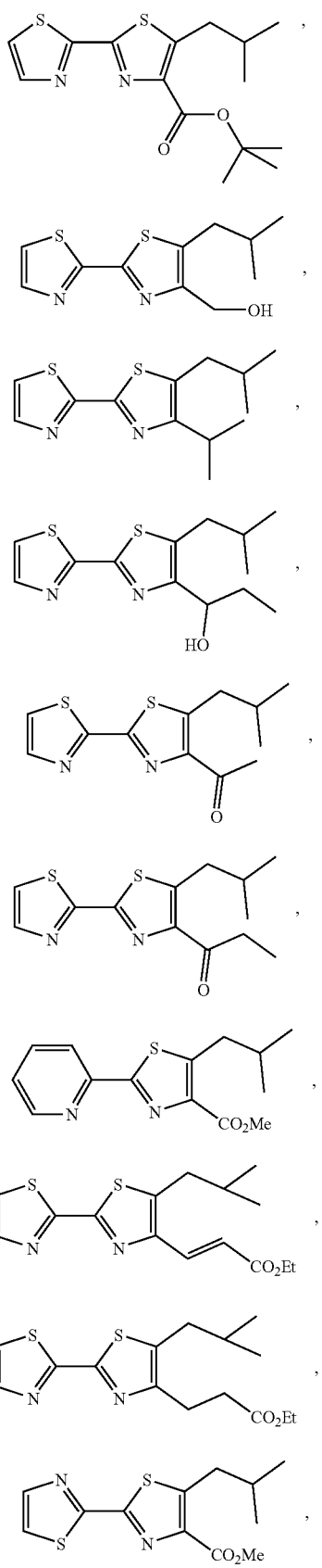
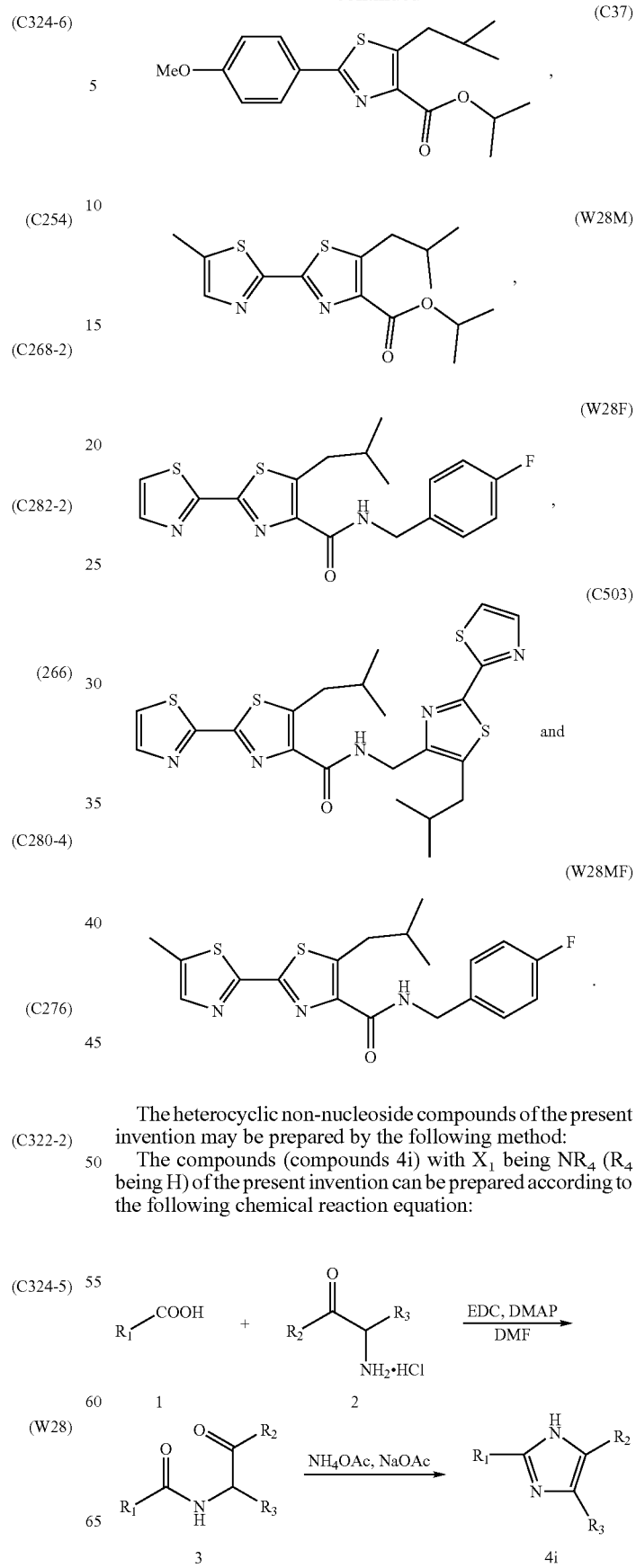
The heterocyclic non-nucleoside compounds of the present invention may be prepared by the following method:
The compounds (compounds 4i) with $X_1$ being $NR_4$ ($R_4$ being H) of the present invention can be prepared according to the following chemical reaction equation:
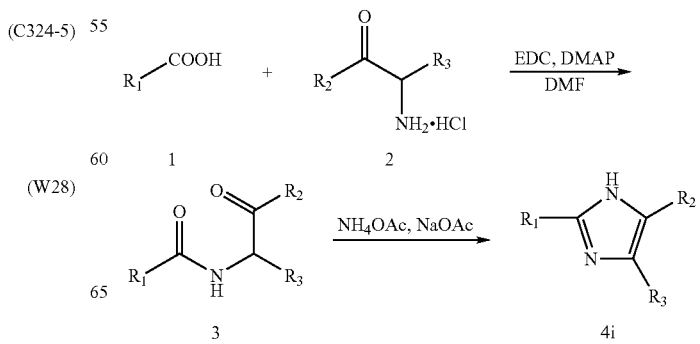

Wherein:

$R_1$ is pyridyl, substituted pyridyl, phenyl, substituted phenyl, 5-membered heterocyclic group, substituted 5-membered heterocyclic group, quinolyl or indolyl, wherein the 5-membered heterocyclic group is a 5-membered heterocyclic group containing one or two hetero atoms selected form N, O and S;

$R_2$ is one selected from the group consisting of $C_1$-$C_{25}$ alkyl; $C_1$-$C_{25}$ alkyl substituted by halogen atom, $C_1$-$C_{25}$ alkyl, $C_3$-$C_{25}$ cycloalkyl, $C_1$-$C_{25}$ alkoxyl, $C_3$-$C_{25}$ cycloalkoxyl, $C_2$-$C_{25}$ alkenyl, $C_3$-$C_{25}$ cycloalkenyl, nitro group, amino group, $C_1$-$C_{25}$ alkylamino group, $C_3$-$C_{25}$ cycloalkylamino group, $C_1$-$C_{25}$ alkyl amide group, hydroxyl, acyloxy or $C_1$-$C_4$ alkoxycarbonyl; $C_3$-$C_9$ cycloalkyl; $C_3$-$C_9$ cycloalkyl substituted by halogen atom, $C_1$-$C_{25}$ alkyl, $C_3$-$C_{25}$ cycloalkyl, $C_1$-$C_{25}$ alkoxyl, $C_3$-$C_{25}$ cycloalkoxyl, $C_2$-$C_{25}$ alkenyl, $C_3$-$C_{25}$ cycloalkenyl, nitro group, amino group, $C_1$-$C_{25}$ alkylamino group, $C_3$-$C_{25}$ cycloalkylamino group, $C_1$-$C_{25}$ alkyl amide group, hydroxyl or acyloxy; aryl; aryl substituted by halogen atom, $C_1$-$C_{25}$ alkyl, $C_3$-$C_{25}$ cycloalkyl, $C_1$-$C_{25}$ alkoxyl, $C_3$-$C_{25}$ cycloalkoxyl, $C_2$-$C_{25}$ alkenyl, $C_3$-$C_{25}$ cycloalkenyl, nitro group, amino group, $C_1$-$C_{25}$ alkylamino group, $C_3$-$C_{25}$ cycloalkylamino group, $C_1$-$C_{25}$ alkyl amide group, hydroxyl or acyloxy; benzyl; benzyl substituted by halogen atom, $C_1$-$C_{25}$ alkyl, $C_3$-$C_{25}$ cycloalkyl, $C_1$-$C_{25}$ alkoxyl, $C_3$-$C_{25}$ cycloalkoxyl, $C_2$-$C_{25}$ alkenyl, $C_3$-$C_{25}$ cycloalkenyl, nitro group, amino group, $C_1$-$C_{25}$ alkylamino group, $C_3$-$C_{25}$ cycloalkylamino group, $C_1$-$C_{25}$ alkyl amide group, hydroxy or acyloxy; $C_2$-$C_{25}$ alkenyl; $C_2$-$C_{25}$ alkenyl substituted by halogen atom, $C_1$-$C_{25}$ alkyl, $C_3$-$C_{25}$ cycloalkyl, $C_1$-$C_{25}$ alkoxyl, $C_3$-$C_{25}$ cycloalkoxyl, nitro group, amino group, $C_1$-$C_{25}$ alkylamino group, $C_3$-$C_{25}$ cycloalkylamino group, $C_1$-$C_{25}$ alkyl amide group, hydroxyl, acyloxy or $C_1$-$C_4$ alkoxycarbonyl; $C_3$-$C_{25}$ cycloalkenyl; $C_3$-$C_{25}$ cycloalkenyl substituted by halogen atom, $C_1$-$C_{25}$ alkyl, $C_3$-$C_{25}$ cycloalkyl, $C_1$-$C_{25}$ alkoxyl, $C_3$-$C_{25}$ cycloalkoxyl, nitro group, amino group, $C_1$-$C_{25}$ alkylamino group, $C_3$-$C_{25}$ cycloalkylamino group, $C_1$-$C_{25}$ alkyl amide group, hydroxyl or acyloxy;

$R_3$ is H, $C_1$-$C_{25}$ alkyl or

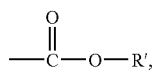

wherein R' is $C_1$-$C_{25}$ alkyl and the like;

Wherein, the compound 1 is commercially available, for example, from Sinopharm Chemical Reagent Co. Ltd. and Aldrich Co. etc. The compound 2 can be synthesized according to prior art of *J. Org. Chem.* 1973; 38; 3571.

In the presence of N-ethyl-N'-(3-dimethylaminopropyl) carbodiimide chloride (EDC), N,N-dimethylpyridine (DMAP) and molecular sieve, in the solvent of DMA, DMF, acetonitrile, dichloromethane or tetrahydrofuran, and under the alkaline condition of pyridine, N-methyl morpholine, triethylamine or diethylpropylethylamine etc., the reaction of the compound 1 and the compound 2 is carried out to produce intermediate compound 3.

Compound 3 is heated to 120-140° C. in the mixture of ammonium acetate and sodium acetate and produces compound 4i through ring closing reaction.

The compounds (compounds 4ii) with $X_1$ being S of the present invention can be prepared according to the following chemical reaction equation:

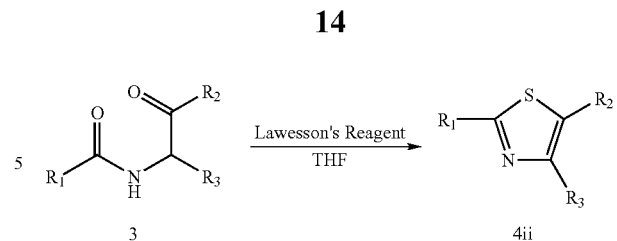

Wherein the Lawesson's reagent is 2,4-bis(para-methoxyphenyl)-1,3-dithio-2,4-bisulfide, which is commercially available. The Lawesson's reagent is added to the above obtained compound 3 in the solvent of tetrahydrofuran, then heated and refluxed to produce the compound 4ii.

The compounds (compounds 4iii) with $X_1$ being O of the present invention can be prepared according to the following chemical reaction equation:

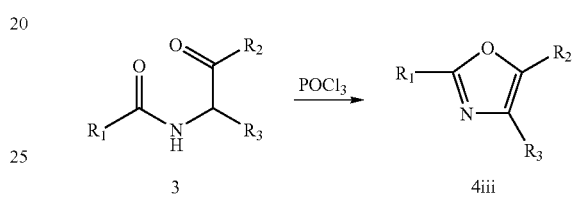

The phosphorus oxychloride solution including the above obtained compound 3 is heated to 100-130□ and reacted to produce the compound 4iii.

The compound 4 with $R_3$ being $CO_2Et$ can react according to the following chemical reaction equation to obtain the compound 5:

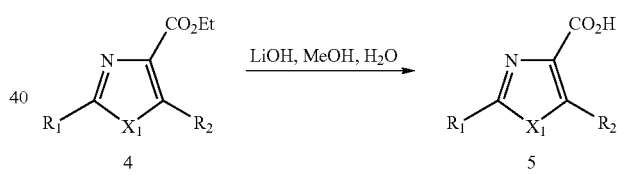

The compound 4 can be the compound 4i, 4ii or 4iii.

Under alkaline condition of lithium hydroxide, sodium hydroxide etc. or under acidic condition of hydrochloric acid, sulfuric acid etc., the compound 4 is hydrolyzed to obtain the compound 5. The condition of the reaction may be room temperature or heated to 100□.

The compound 6 can be prepared from the compound 5 according to the following chemical reaction equation:

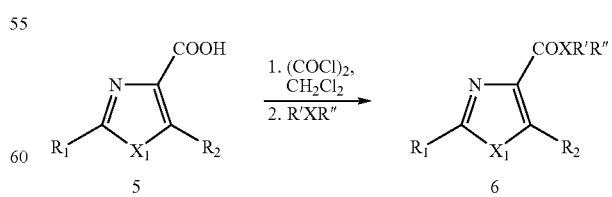

Wherein each R' and R" independently is hydrogen atom, $C_1$-$C_{25}$ alkyl, halogenated $C_1$-$C_{10}$ alkyl, aryl, benzyl, substituted benzyl, $C_1$-$C_6$ hydroxyalkyl, substituted or unsubstituted heterocyclomethylene, wherein the substituent on benzyl group may be halogen, $C_1$-$C_{10}$ alkyl, $C_1$-$C_{10}$ alkoxyl, $C_1$-$C_{10}$ alkylamino group, nitrile group, carboxyl or $C_1$-$C_{10}$ alkyloxycarbonyl; X is O or NH.

The compound 5 is transformed into acyl chloride under the condition of oxalyl chloride or thionyl chloride etc, and then acyl chloride is reacted with various alcohols, various substituted amine or aqueous ammonia etc. to produce the compound 6. The solvent of the reaction may be dichloromethane, ethyl acetate, water or the mixture thereof. The reaction is conducted under alkaline condition, and the alkaline reagent may be inorganic alkali such as potassium carbonate, potassium bicarbonate, sodium carbonate or sodium bicarbonate etc., or organic alkali such as pyridine, N-methylmorpholine, isobutyl chloroformate, triethylamine and diethylpropylethylamine etc.

Or the compound 7 can be prepared from the compound 4 according to the following chemical reaction equation:

Wherein, the compound 4 reacted to produce compound 7 by adding aluminum lithium hydride in the organic solvent of anhydrous tetrahydrofuran or absolute ether etc. under the temperature of –20□-25□.

Or the compound 8 can be prepared from the compound 7 according to the following chemical reaction equation:

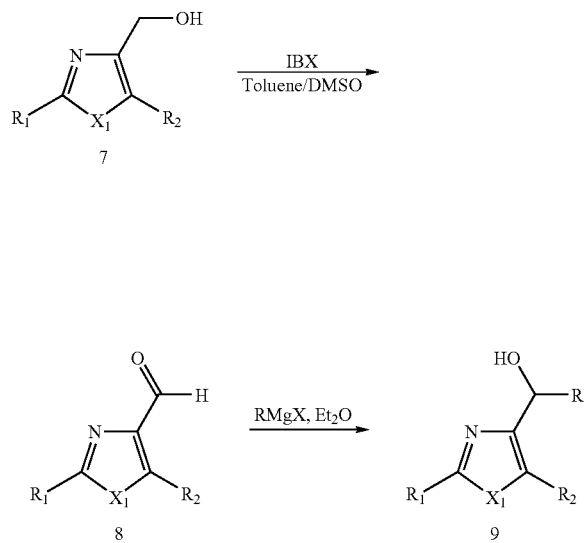

Wherein, IBX is 2-iodoxybenzoic acid, which is purchased from Aldrich Co. The Grignard reagent is $C_1$-$C_{25}$ alkyl or $C_3$-$C_8$ cycloalkyl Grignard reagent, i.e., R is $C_1$-$C_{25}$ alkyl or $C_3$-$C_8$ cycloalkyl. The compound 7 is oxidized to produce intermediate compound 8. The compound 8 reacted to produce the compound 9 by adding Grignard reagent in solvent of absolute ether or anhydrous tetrahydrofuran. The compound 4 can also conduct this reaction instead of the compound 8.

Or the compound 10 can be prepared from the compound 9 according to the following chemical reaction equation:

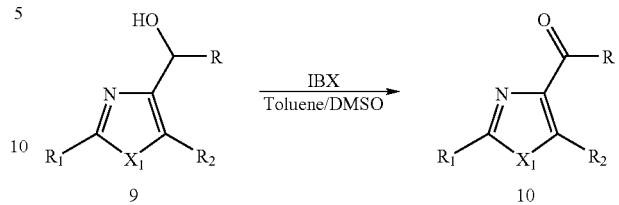

The compound 9 can be oxidized to produce the compound 10 by using the active $MnO_2$ in acetone solution or IBX in the mixed solution of toluene and DMSO etc.

Or the compound 19 can be prepared according to the following chemical reaction equation:

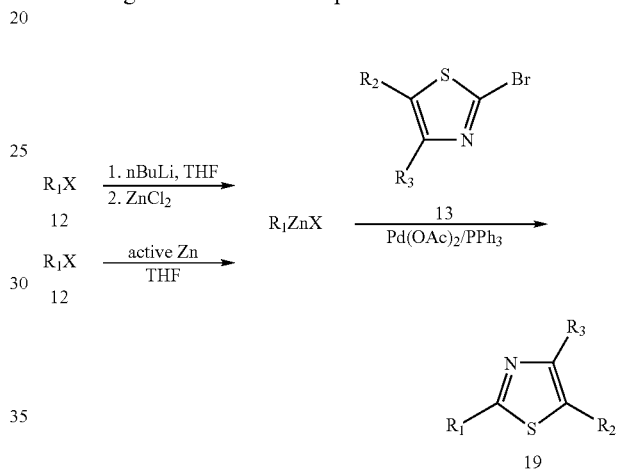

Wherein, $R_1$, $R_2$, $R_3$ are defined as same as above, X is halogen. The synthesis of the compound 13 can refer to the prior art (*J. Chem. Soc. Perkin I.* 1982, 159-164; Heterocyclic. Chem. 1991, 28, 1003). The compound 12 reacted for 0.5-2 hours by adding butyllithium in organic solvent of anhydrous tetrahydrofuran or absolute ether, after that, anhydrous zinc chloride is added to produce zincon. Or, active zinc powder is added into the organic solvent of anhydrous tetrahydrofuran or absolute ether including compound 12 and the above mixture is heated and refluxed to produce zincon. And then the compound 13 is added and react for 8-24 hours to obtain the compound 19 in the solvent of benzene or toluene and the like, under the presence of the palladium catalyst (tetra(triphenylphosphine)palladium, or the mixture of palladium acetate and triphenyl phosphine).

Or the compound 14 and the compound 15 can be prepared according to the following chemical reaction equation:

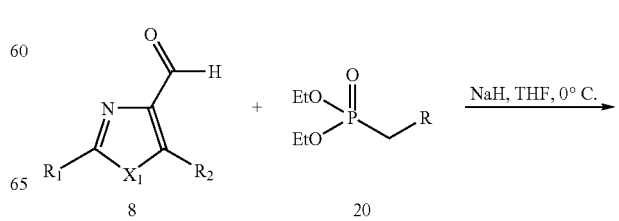

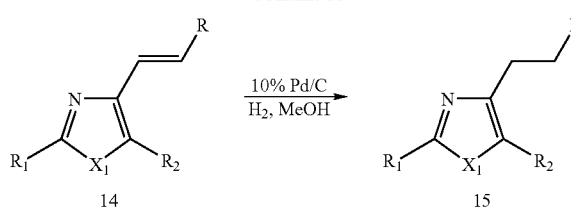

Wherein, R is $C_1$-$C_{25}$ alkyl, phenyl or

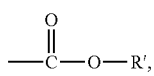

wherein R' is $C_1$-$C_{25}$ alkyl etc. The compound 20 is commercially available, e.g. from Sinopharm Chemical Reagent Co. Ltd, Aldrich Co. etc. The compound 8 and the compound 20 react to produce the compound 14 in anhydrous tetrahydrofuran solution by adding NaH, and the compound 14 is hydrogenated to obtain the compound 15.

Or the compound 16 can be prepared according to the following chemical reaction equation:

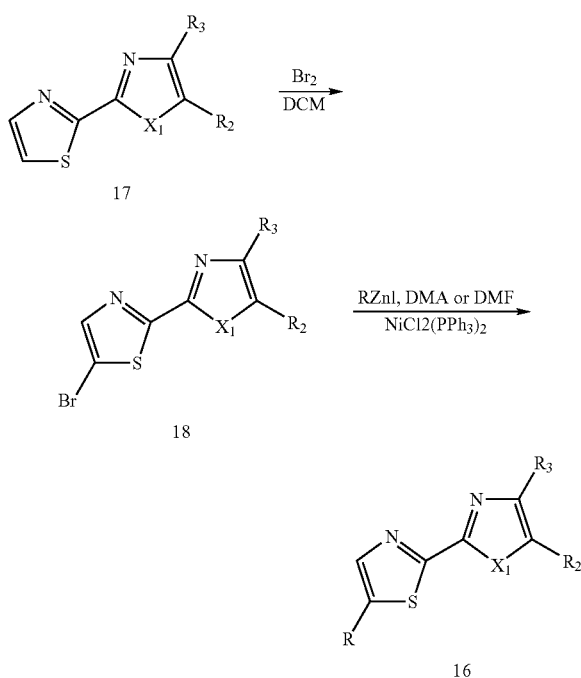

Wherein, the compound 17 is the compound 4 with $R_1$ being 2-thiazolyl; $R_2$, $R_3$ are defined as same as above; R is $C_1$-$C_{25}$ alkyl or $C_3$-$C_8$ cycloalkyl. The compound 17 reacted for 24 hours to produce compound 18 in dichloromethane solution by adding liquid bromine. The compound 18 reacts under room temperature to produce compound 16 in the solvent of DMA or DMF by adding the zincon and catalyst nickel.

Or the compound 19 can be prepared according to the following chemical reaction equation:

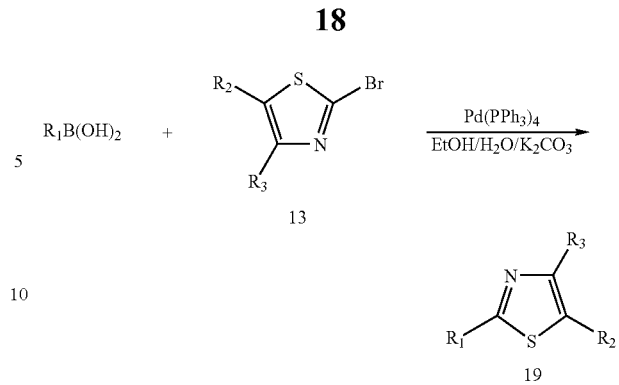

Wherein, $R_1$, $R_2$, $R_3$ are defined as same as above. The boron reagent can be commercially available, e.g. from Sinopharm Chemical Reagent Co. Ltd, Aldrich Co. etc. The synthesis method of the compound 13 can refer to the prior art (*J. Chem. Soc. Perkin I.* 1982, 159-164; Heterocyclic. Chem. 1991, 28, 1003). The boron reagent and the compound 13 react for 12 hours to obtain compound 19 in the solvent of methanol or ethanol by adding palladium catalyst, water and alkali of potassium carbonate or sodium carbonate.

Or the compound 21 can be prepared according to the following chemical reaction equation:

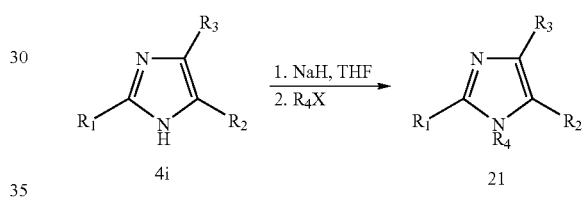

Wherein, $R_4$ is aryl, substituted aryl, benzyl, $C_1$-$C_{13}$ alkyl, substituted $C_1$-$C_{13}$ alkyl, $C_2$-$C_6$ alkenyl or $C_3$-$C_6$ cycloalkyl, wherein the substituent(s) on the said aryl or $C_1$-$C_{13}$ alkyl may be halogen atom, alkoxyl, amino group, alkylamino group or hydroxyl; X is halogen atom.

The compound 4i reacts for 1 hour at room temperature by adding NaH in anhydrous tetrahydrofuran solution, and then halide is added and reacts for 12 hours to obtain compound 21.

Generally TLC is used to detect the completion degree of the reaction. After the reaction completed, the reaction is typically quenched with ice-water, and the resultant mixture is extracted with ethylether, ethyl acetate, dichloromethane, trichloromethane etc., and washed with 5% hydrochloric acid, water, saturated brine in sequence, then dried, and the solvent is removed under reduced pressure at low temperature. The final product is obtained through column chromatography and is identified by the methods of nuclear magnetic resonance (NMR), mass spectrum and the like.

The present invention provides an antiviral pharmaceutical composition, which contains one or more of the above heterocyclic non-nucleoside compounds as active compounds, and may further contains pharmaceutically conventional adjuvant, such as excipient, disintegrant, anti-oxidant, sweetening agent, coating agent etc.

Advantageous Effect

The present invention designs and synthesizes a kind of new heterocyclic non-nucleoside antiviral agents, which can effectively inhibit the replication of influenza virus, the DNA replication of hepatitis B virus (HBV), and the formation of HBsAg and HBeAg. These compounds can be used for the preparation of medicaments for treating viral diseases, and may overcome the disadvantages of the known nucleosides drugs, including cytotoxicity, and the requirement of other drugs having different structure against the drug-resistant virus variants induced by long-term medication. The structure of the compounds according to the invention is relatively simple and easy to be prepared.

DESCRIPTION OF THE DRAWING

FIG. 1 is the comparison of the inhibition ratios of DHBV-DNA level in duck serum of the treating group and that of the control group with viral infection, after the duck hepatitis B virus infected ducks were orally (intragastric) administrated.

BEST MODE OF THE INVENTION

The present invention will be further described in conjugation with the following specific examples, but the present invention is not limited thereto.

PREPARATION EXAMPLES

In the following preparation examples, NMR was measured using Mercury-Vx 300M produced by Varian, and the NMR calibration was: δH/C 7.26/77.0 ppm (CDCl$_3$). The reagents were provided mainly by Shanghai Chemical Reagent Co., Ltd. The purification of the products were performed mainly with column chromatography of silica gel (200-300 mesh). And the type of the silica gel used in column chromatography was coarse hollow (ZLX-□), which was produced by the Branch of Qingdao Haiyang Chemical Plant.

Preparation Example 1

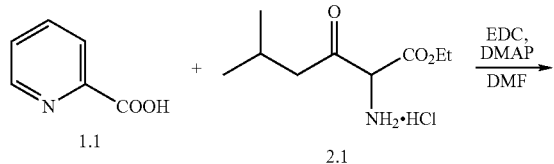

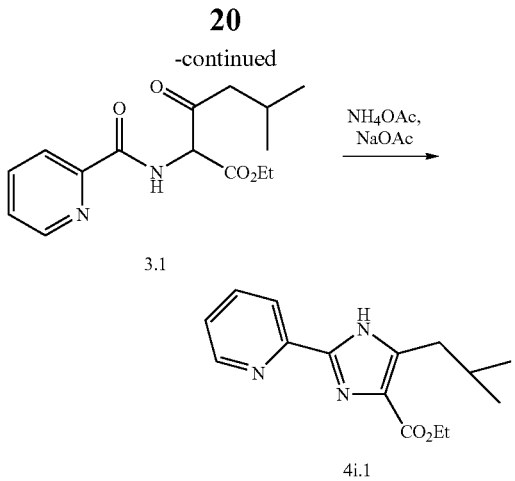

The compound 1.1 (3.3 mmol), the compound 2.1 (3 mmol), N-ethyl-N'-(3-dimethylaminopropyl) carbodiimide hydrochloride (EDC) (3.3 mmol), N,N-dimethylpyridine (DMAP) (0.3 mmol) and molecular sieve were mixed, and cooled in ice bath (0□). Then DMF (5 mL), pyridine (4.5 mmol) were added sequentially. The completion degree of the reaction was tracked by TLC. After the reaction was completed, the reaction solution was diluted with water (25 mL), extracted with EtOAc (25 mL). The solvent was removed completely by concentration. Then the compound 3.1 was obtained by separation through column chromatography with petroleum ether/ethyl acetate (volume ratio 5:1). Then the compound 3.1 (0.6 mmol) was mixed with ammonium acetate (NH$_4$OAc) (15 mmol), sodium acetate (NaOAc) (30 mmol) and heated to 130□. The completion degree of the reaction was tracked by TLC. Then the reaction solution was cooled to room temperature and diluted with water (50 mL), extracted with ethyl acetate (50 mL). The solvent was removed completely by concentration. Then the compound 4i.1 was obtained by separation through column chromatography with petroleum ether/ethyl acetate (volume ratio 1:1).

Except pyridine-2-carboxylic acid was replaced by the substituted carboxylic acid (compound 1) listed in the following table and the compound 2.1 was replaced by various compound 2, the following compounds were synthesized by the same method as preparation example 1:

| Compound 4i | Compound 1 | Compound 2 | Structure formula of compound 4i | $^1$H NMR (CDCl$_3$, 300 MHz) data |
|---|---|---|---|---|
| C273 | pyridine-2-COOH | EtO$_2$C-CH(NH$_2$·HCl)-CH$_2$-C(O)-CH$_2$-CH(CH$_3$)$_2$ | 2-pyridyl-imidazole with isobutyl and CO$_2$Et | δ 0.97 (d, J = 6.6 Hz, 6H), 1.42 (t, J = 7.2 Hz, 3H), 2.06 (m, 1H), 2.88 (d, J = 7.2 Hz, 2H), 4.39 (q, J = 7.2 Hz, 2H), 7.31 (t, J = 9.0 Hz, 1H), 7.83 (t, J = 7.8 Hz, 1H), 8.28 (d, J = 7.8 Hz, 1H), 8.53 (d, J = 4.2 Hz, 1H). |
| C311-2 | indole-2-COOH | EtO$_2$C-CH(NH$_2$·HCl)-CH$_2$-C(O)-CH$_2$-CH(CH$_3$)$_2$ | 2-indolyl-imidazole with isobutyl and CO$_2$Et | δ 1.04 (d, J = 6.6 Hz, 6H), 1.44 (t, J = 7.2 Hz, 3H), 2.02 (m, 1H), 2.94 (d, J = 7.2 Hz, 2H), 4.34 (q, J = 6.9 Hz, 2H), 7.11 (s, 1H), 7.21 (t, J = 7.2 Hz, 1H), 7.26 (t, J = 7.2 Hz, 1H), 7.48 (d, J = 3.3 Hz, 1H), 7.56 (d, J = 7.8 Hz, 1H), 10.90 (br, 1H). |

-continued

| Compound 4i | Compound 1 | Compound 2 | Structure formula of compound 4i | $^1$H NMR (CDCl$_3$, 300 MHz) data |
|---|---|---|---|---|
| C323-2 | quinoline-2-COOH | EtO$_2$C-CH(NH$_2$·HCl)-C(=O)-CH$_2$CH(CH$_3$)$_2$ | quinolin-2-yl imidazole with isobutyl and CO$_2$Et | δ 0.94 (d, J = 6.6 Hz, 6H), 1.36 (t, J = 7.2 Hz, 3H), 1.92 (m, 1H), 2.75 (d, J = 7.2 Hz, 2H), 4.35 (q, J = 6.9 Hz, 2H), 7.50 (t, J = 7.8 Hz, 1H), 7.64 (t, J = 6.9 Hz, 1H), 7.79 (d, J = 7.8 Hz, 1H), 7.94 (d, J = 8.4 Hz, 1H), 8.23 (d, J = 8.1 Hz, 1H), 8.42 (d, J = 8.4 Hz, 1H). |
| C305-2 | thiazole-2-COOH | EtO$_2$C-CH(NH$_2$·HCl)-C(=O)-cyclohexyl | thiazol-2-yl imidazole with cyclohexyl and CO$_2$Et | δ 0.95 m, 6H), 1.70 (m, 5H), 1.96 (m, 2H), 3.20 (m, 1H), 4.37 (t, 2H), 7.36 (d, 1H), 7.80 (d, 1H), 11.10 (bs, 1H). |

Preparation Example 2

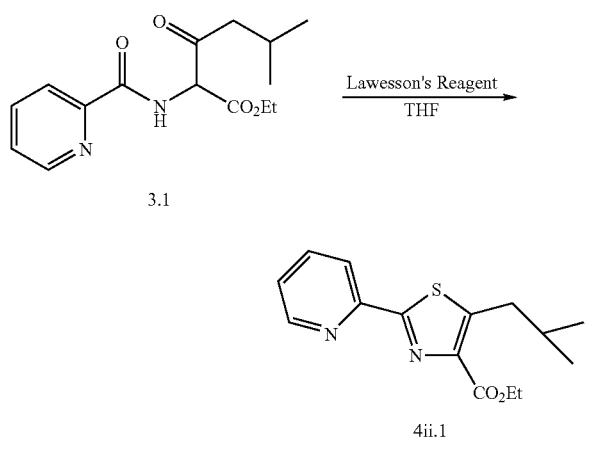

The compound 3.1 (0.6 mmol) and Lawesson's reagent (0.9 mmol) were mixed, then after adding THF (5 mL), heated and refluxed. The completion degree of the reaction was tracked by TLC. Subsequently the reaction solution was cooled to room temperature, and concentrated to remove the solvent completely. The compound 4ii.1 was obtained by separation through column chromatography with petroleum ether/ethyl acetate (volume ratio 3:1).

Except pyridine-2-carboxylic acid was replaced by the substituted carboxylic acid (compound 1) listed in the following table and the compound 2.1 was replaced by the different compound 2, the various compound 3 can be synthesized by the same method as preparation example 1. Then the following target compounds were synthesize by the same method as preparation example 2:

| compound 4ii | compound 1 | compound 2 | structure formula of compound 4ii | $^1$H NMR (CDCl$_3$, 300 MHz) data |
|---|---|---|---|---|
| C290 | pyridine-2-COOH | EtO$_2$C-CH(NH$_2$·HCl)-C(=O)-CH$_2$CH(CH$_3$)$_2$ | pyridin-2-yl thiazole with isobutyl and CO$_2$Et | δ 0.92 (d, J = 6.6 Hz, 6H), 1.35 (t, J = 7.2 Hz, 3H), 1.94 (m, 1H), 3.07 (d, J = 7.2 Hz, 2H), 4.36 (q, J = 7.2 Hz, 2H), 7.22 (t, J = 5.1 Hz, 1H), 7.69 (t, J = 1.8 Hz, 1H), 8.17 (d, J = 7.5 Hz, 1H), 8.48 (d, J = 4.2 Hz, 1H). |
| W28 | thiazole-2-COOH | MeO$_2$C-CH(NH$_2$·HCl)-C(=O)-CH$_2$CH(CH$_3$)$_2$ | thiazol-2-yl thiazole with isobutyl and COOMe | δ 0.99 (d, 6H), 1.99 (m, 1H), 3.15 (d, 2H), 3.96 (s, 3H), 7.46 (d, 1H), 7.86 (d, 1H). |

-continued

| compound 4ii | compound 1 | compound 2 | structure formula of compound 4ii | $^1$H NMR (CDCl$_3$, 300 MHz) data |
|---|---|---|---|---|
| C328-2 | 1H-indole-2-carboxylic acid | ethyl 2-amino-5-methyl-3-oxohexanoate·HCl | ethyl 5-isobutyl-2-(1H-indol-2-yl)thiazole-4-carboxylate | δ 1.04 (d, J = 6.6 Hz, 6H), 1.28 (t, J = 7.2 Hz, 3H), 2.02 (m, 1H), 3.16 (d, J = 7.2 Hz, 2H), 4.34 (q, J = 6.9 Hz, 2H), 6.94 (s, 1H), 7.10 (t, J = 6.9 Hz, 1H), 7.21 (m, 2H), 7.62 (d, J = 8.1 Hz, 1H), 10.17 (br, 1H). |
| C340 | quinoline-2-carboxylic acid | ethyl 2-amino-5-methyl-3-oxohexanoate·HCl | ethyl 5-isobutyl-2-(quinolin-2-yl)thiazole-4-carboxylate | δ 1.02 (d, J = 6.6 Hz, 6H), 1.36 (t, J = 7.2 Hz, 3H), 2.06 (m, 1H), 3.18 (d, J = 7.2 Hz, 2H), 4.45 (q, J = 6.9 Hz, 2H), 7.53 (t, J = 7.8 Hz, 1H), 7.71 (t, J = 6.9 Hz, 1H), 7.80 (d, J = 7.8 Hz, 1H), 8.08 (d, J = 8.4 Hz, 1H), 8.22 (d, J = 8.1 Hz, 1H), 8.38 (d, J = 8.4 Hz, 1H). |
| C289 | benzoic acid | ethyl 2-amino-5-methyl-3-oxohexanoate·HCl | ethyl 5-isobutyl-2-phenylthiazole-4-carboxylate | δ 0.98 (d, J = 6.6 Hz, 6H), 1.40 (t, J = 7.2 Hz, 3H), 1.97 (m, 1H), 3.11 (d, J = 7.2 Hz, 2H), 4.45 (q, J = 6.9 Hz, 2H), 7.38 (br, 3H), 7.92 (br, 2H). |
| C290-2 | nicotinic acid | ethyl 2-amino-5-methyl-3-oxohexanoate·HCl | ethyl 5-isobutyl-2-(pyridin-3-yl)thiazole-4-carboxylate | δ 0.98 (d, J = 6.6 Hz, 6H), 1.41 (t, J = 7.2 Hz, 3H), 1.98 (m, 1H), 3.13 (d, J = 7.2 Hz, 2H), 4.41 (q, J = 7.2 Hz, 2H), 7.35 (dd, J1 = 5.1 Hz, J2 = 4.8 Hz, 1H), 8.24 (d, J = 8.1 Hz, 1H), 8.62 (d, J = 4.8 Hz, 1H), 9.09 (s, 1H). |
| C290-3 | isonicotinic acid | ethyl 2-amino-5-methyl-3-oxohexanoate·HCl | ethyl 5-isobutyl-2-(pyridin-4-yl)thiazole-4-carboxylate | δ 0.95 (d, J = 6.6 Hz, 6H), 1.38 (t, J = 7.2 Hz, 3H), 1.94 (m, 1H), 3.10 (d, J = 7.2 Hz, 2H), 4.38 (q, J = 7.2 Hz, 2H), 7.75 (dd, J = 4.8 Hz, 2H), 8.63 (d, J = 4.5 Hz, 1H). |
| C306-3 | 3-hydroxypicolinic acid | ethyl 2-amino-5-methyl-3-oxohexanoate·HCl | ethyl 2-(3-hydroxypyridin-2-yl)-5-isobutylthiazole-4-carboxylate | δ 1.02 (d, J = 6.6 Hz, 6H), 1.43 (t, J = 7.2 Hz, 3H), 2.05 (m, 1H), 3.18 (d, J = 7.2 Hz, 2H), 4.40 (q, J = 7.2 Hz, 2H), 7.27 (t, J = 5.1 Hz, 1H), 7.49 (d, J = 3.3 Hz, 1H), 8.16 (d, J = 4.5 Hz, 1H), 11.72 (bs, 1H). |
| C306-2 | 6-hydroxypicolinic acid | ethyl 2-amino-5-methyl-3-oxohexanoate·HCl | ethyl 2-(6-hydroxypyridin-2-yl)-5-isobutylthiazole-4-carboxylate | δ 0.94 (d, J = 6.6 Hz, 6H), 1.42 (t, J = 7.2 Hz, 3H), 1.93 (m, 1H), 3.08 (d, J = 7.2 Hz, 2H), 4.42 (q, J = 7.2 Hz, 2H), 7.67 (m, 2H), 8.06 (d, J = 7.5 Hz, 1H). |
| C218 | picolinic acid | 1-amino-5-methylhexan-2-one·HCl | 5-isobutyl-2-(pyridin-2-yl)thiazole | δ 0.98 (d, J = 6.6 Hz, 6H), 1.93 (m, 1H), 2.74 (d, J = 7.2 Hz, 2H), 7.28 (q, J = 5.7 Hz, 2H), 7.57 (s, 1H), 7.77 (t, J = 7.8 Hz, 1H), 8.14 (d, J = 8.1 Hz, 1H), 8.59 (d, J = 4.8 Hz, 1H). |

-continued

| compound 4ii | compound 1 | compound 2 | structure formula of compound 4ii | $^1$H NMR (CDCl$_3$, 300 MHz) data |
|---|---|---|---|---|
| C375 | 5-bromothiazole-2-carboxylic acid | ethyl 2-amino-5-methyl-3-oxohexanoate·HCl | ethyl 5′-bromo-5-isobutyl-[2,2′-bithiazole]-4-carboxylate | δ 1.00 (d, J = 6.6 Hz, 6H), 1.44 (t, J = 7.2 Hz, 3H), 2.00 (m, 1H), 3.15 (d, J = 7.2 Hz, 2H), 4.42 (q, J = 6.9 Hz, 2H), 7.74 (s, 1H). |
| C307-2 | 4-fluorobenzoic acid | ethyl 2-amino-5-methyl-3-oxohexanoate·HCl | ethyl 2-(4-fluorophenyl)-5-isobutylthiazole-4-carboxylate | δ 0.96 (d, J = 6.6 Hz, 6H), 1.39 (t, J = 7.2 Hz, 3H), 1.95 (m, 1H), 3.09 (d, J = 7.2 Hz, 2H), 4.39 (q, J = 7.2 Hz, 2H), 7.07 (m, 2H), 7.88 (m, 2H). |
| C307-3 | 3-fluorobenzoic acid | ethyl 2-amino-5-methyl-3-oxohexanoate·HCl | ethyl 2-(3-fluorophenyl)-5-isobutylthiazole-4-carboxylate | δ 0.94 (d, J = 6.6 Hz, 6H), 1.38 (t, J = 7.2 Hz, 3H), 1.94 (m, 1H), 3.08 (d, J = 7.2 Hz, 2H), 4.37 (q, J = 7.2 Hz, 2H), 7.06 (m, 1H), 7.33 (m, 1H), 7.63 (m, 2H). |
| C307-4 | 2-fluorobenzoic acid | ethyl 2-amino-5-methyl-3-oxohexanoate·HCl | ethyl 2-(2-fluorophenyl)-5-isobutylthiazole-4-carboxylate | δ 1.00 (d, J = 6.6 Hz, 6H), 1.45 (t, J = 7.2 Hz, 3H), 2.02 (m, 1H), 3.15 (d, J = 7.5 Hz, 2H), 4.44 (q, J = 7.2 Hz, 2H), 7.22 (m, 2H), 7.40 (m, 1H), 8.34 (m, 1H). |
| C319-3 | 4-methoxybenzoic acid | ethyl 2-amino-5-methyl-3-oxohexanoate·HCl | ethyl 5-isobutyl-2-(4-methoxyphenyl)thiazole-4-carboxylate | δ 0.97 (d, J = 6.6 Hz, 6H), 1.41 (t, J = 7.2 Hz, 3H), 1.96 (m, 1H), 3.09 (d, J = 7.2 Hz, 2H), 3.82 (s, 3H), 4.40 (q, J = 7.2 Hz, 2H), 6.91 (d, J = 8.7 Hz, 2H), 7.85 (d, J = 8.4 Hz, 2H). |
| C319-4 | 3-methoxybenzoic acid | ethyl 2-amino-5-methyl-3-oxohexanoate·HCl | ethyl 5-isobutyl-2-(3-methoxyphenyl)thiazole-4-carboxylate | δ 1.00 (d, J = 6.6 Hz, 6H), 1.44 (t, J = 7.2 Hz, 3H), 1.99 (m, 1H), 3.13 (d, J = 7.2 Hz, 2H), 3.87 (s, 3H), 4.43 (q, J = 7.2 Hz, 2H), 6.95 (d, J = 8.4 Hz, 1H), 7.34 (t, J = 8.4 Hz, 1H), 7.49 (d, J = 7.8 Hz, 1H), 7.52 (s, 1H). |
| C319-5 | 2-methoxybenzoic acid | ethyl 2-amino-5-methyl-3-oxohexanoate·HCl | ethyl 5-isobutyl-2-(2-methoxyphenyl)thiazole-4-carboxylate | δ 0.99 (d, J = 6.6 Hz, 6H), 1.44 (t, J = 7.2 Hz, 3H), 2.03 (m, 1H), 3.14 (d, J = 7.2 Hz, 2H), 3.99 (s, 3H), 4.43 (q, J = 7.2 Hz, 2H), 6.98 (d, J = 8.4 Hz, 1H), 7.07 (t, J = 7.5 Hz, 1H), 7.35 (t, J = 8.1 Hz, 1H), 8.45 (d, J = 7.8 Hz, 1H). |
| C334-2 | 4-nitrobenzoic acid | ethyl 2-amino-5-methyl-3-oxohexanoate·HCl | ethyl 5-isobutyl-2-(4-nitrophenyl)thiazole-4-carboxylate | δ 0.99 (d, J = 6.6 Hz, 6H), 1.42 (t, J = 7.2 Hz, 3H), 1.98 (m, 1H), 3.14 (d, J = 7.2 Hz, 2H), 4.42 (q, J = 7.2 Hz, 2H), 8.08 (d, J = 6.9 Hz, 2H), 8.25 (d, J = 6.9 Hz, 2H). |

-continued

| compound 4ii | compound 1 | compound 2 | structure formula of compound 4ii | $^1$H NMR (CDCl$_3$, 300 MHz) data |
|---|---|---|---|---|
| C334-3 | 3-nitrobenzoic acid (O$_2$N-C$_6$H$_4$-COOH, meta) | EtO$_2$C-CH(NH$_2$·HCl)-C(O)-CH$_2$-CH(CH$_3$)$_2$ | 2-(3-nitrophenyl)-5-isobutyl-thiazole-4-carboxylic acid ethyl ester | δ 0.96 (d, J = 6.6 Hz, 6H), 1.40 (t, J = 7.2 Hz, 3H), 1.95 (m, 1H), 3.11 (d, J = 7.2 Hz, 2H), 4.38 (q, J = 7.2 Hz, 2H), 7.58 (t, J = 8.1 Hz, 1H), 8.21 (t, J = 7.5 Hz, 2H), 8.68 (s, 1H). |
| C334-4 | 2-nitrobenzoic acid | EtO$_2$C-CH(NH$_2$·HCl)-C(O)-CH$_2$-CH(CH$_3$)$_2$ | 2-(2-nitrophenyl)-5-isobutyl-thiazole-4-carboxylic acid ethyl ester | δ 1.01 (d, J = 6.6 Hz, 6H), 1.40 (t, J = 7.2 Hz, 3H), 2.00 (m, 1H), 3.17 (d, J = 7.5 Hz, 2H), 4.39 (q, J = 7.2 Hz, 2H), 7.66 (m, 3H), 7.93 (d, J = 7.8 Hz, 1H). |
| C404 | BocHN-C$_6$H$_4$-COOH (para) | EtO$_2$C-CH(NH$_2$·HCl)-C(O)-CH$_2$-CH(CH$_3$)$_2$ | 2-(4-BocNH-phenyl)-5-isobutyl-thiazole-4-carboxylic acid ethyl ester | δ 0.96 (d, J = 6.6 Hz, 6H), 1.38 (t, J = 7.2 Hz, 3H), 1.45 (s, 9H), 1.95 (m, 1H), 3.09 (d, J = 6.9 Hz, 2H), 4.38 (q, J = 7.2 Hz, 2H), 7.11 (s, 1H), 7.44 (d, J = 8.7 Hz, 2H), 7.81 (d, J = 8.4 Hz, 2H). |
| C323-3 | 3-chlorobenzoic acid | EtO$_2$C-CH(NH$_2$·HCl)-C(O)-CH$_2$-CH(CH$_3$)$_2$ | 2-(3-chlorophenyl)-5-isobutyl-thiazole-4-carboxylic acid ethyl ester | δ 1.00 (d, J = 6.6 Hz, 6H), 1.44 (t, J = 7.2 Hz, 3H), 1.99 (m, 1H), 3.14 (d, J = 7.2 Hz, 2H), 4.44 (q, J = 7.2 Hz, 2H), 7.37 (m, 2H), 7.77 (d, J = 6.9 Hz, 1H), 7.96 (s, 1H). |
| C358 | 5-phenyl-thiazole-2-carboxylic acid | EtO$_2$C-CH(NH$_2$·HCl)-C(O)-CH$_2$-CH(CH$_3$)$_2$ | 5-phenyl-[2,2'-bithiazole]-5'-isobutyl-4'-carboxylic acid ethyl ester | δ 1.02 (d, J = 6.6 Hz, 6H), 2.02 (m, 1H), 3.18 (d, J = 7.2 Hz, 2H), 3.97 (s, 3H), 7.44 (m, 3H), 7.62 (d, J = 8.1 Hz, 2H), 8.03 (s, 1H). |
| C303-1 | 4-methylbenzoic acid | EtO$_2$C-CH(NH$_2$·HCl)-C(O)-CH$_2$-CH(CH$_3$)$_2$ | 2-(4-methylphenyl)-5-isobutyl-thiazole-4-carboxylic acid ethyl ester | δ 0.99 (d, J = 6.6 Hz, 6H), 1.43 (t, J = 7.2 Hz, 3H), 1.99 (m, 1H), 2.36 (s, 3H), 3.12 (d, J = 7.2 Hz, 2H), 4.42 (q, J = 7.2 Hz, 2H), 7.20 (d, J = 8.1 Hz, 2H), 7.82 (d, J = 8.4 Hz, 2H). |
| C303-2 | 3-methylbenzoic acid | EtO$_2$C-CH(NH$_2$·HCl)-C(O)-CH$_2$-CH(CH$_3$)$_2$ | 2-(3-methylphenyl)-5-isobutyl-thiazole-4-carboxylic acid ethyl ester | δ 1.00 (d, J = 6.6 Hz, 6H), 1.44 (t, J = 7.2 Hz, 3H), 1.99 (m, 1H), 2.39 (s, 3H), 3.13 (d, J = 7.2 Hz, 2H), 4.43 (q, J = 7.2 Hz, 2H), 7.21 (d, J = 7.5 Hz, 1H), 7.29 (t, J = 7.8 Hz, 1H), 7.70 (d, J = 7.8 Hz, 1H), 7.80 (s, 1H). |
| C303-3 | 2-methylbenzoic acid | EtO$_2$C-CH(NH$_2$·HCl)-C(O)-CH$_2$-CH(CH$_3$)$_2$ | 2-(2-methylphenyl)-5-isobutyl-thiazole-4-carboxylic acid ethyl ester | δ 0.99 (d, J = 6.6 Hz, 6H), 1.40 (t, J = 7.2 Hz, 3H), 2.00 (m, 1H), 2.55 (s, 3H), 3.15 (d, J = 7.2 Hz, 2H), 4.40 (q, J = 7.2 Hz, 2H), 7.24 (m, 3H), 7.64 (d, J = 7.5 Hz, 1H). |

-continued

| compound 4ii | compound 1 | compound 2 | structure formula of compound 4ii | $^1$H NMR (CDCl$_3$, 300 MHz) data |
|---|---|---|---|---|
| C364-2 | MeO, O$_2$N-phenyl-COOH | EtO$_2$C-CH(NH$_2$·HCl)-C(O)-CH$_2$-CH(CH$_3$)$_2$ | MeO, O$_2$N-phenyl-thiazole(isobutyl)(CO$_2$Et) | δ 1.01 (d, J = 6.6 Hz, 6H), 1.45 (t, J = 7.2 Hz, 3H), 2.01 (m, 1H), 3.16 (d, J = 7.2 Hz, 2H), 4.08 (s, 3H), 4.45 (q, J = 7.2 Hz, 2H), 7.50 (d, J = 8.4 Hz, 1H), 7.75 (s, 1H), 7.92 (d, J = 8.4 Hz, 1H). |
| C305-4 | HO-phenyl-COOH | EtO$_2$C-CH(NH$_2$·HCl)-C(O)-CH$_2$-CH(CH$_3$)$_2$ | HO-phenyl-thiazole(isobutyl)(CO$_2$Et) | δ 0.99 (d, J = 6.6 Hz, 6H), 1.34 (t, J = 7.2 Hz, 3H), 1.98 (m, 1H), 2.36 (s, 3H), 3.10 (d, J = 7.2 Hz, 2H), 4.35 (q, J = 7.2 Hz, 2H), 6.80 (d, J = 8.7 Hz, 2H), 7.78 (d, J = 9.0 Hz, 2H), 8.11 (s, 1H). |
| C364-1 | O$_2$N, OMe-phenyl-COOH | EtO$_2$C-CH(NH$_2$·HCl)-C(O)-CH$_2$-CH(CH$_3$)$_2$ | O$_2$N, OMe-phenyl-thiazole(isobutyl)(CO$_2$Et) | δ 0.96 (d, J = 6.6 Hz, 6H), 1.39 (t, J = 7.2 Hz, 3H), 1.95 (m, 1H), 3.12 (d, J = 7.2 Hz, 2H), 3.90 (s, 3H), 4.35 (q, J = 7.2 Hz, 2H), 7.10 (d, J = 7.8 Hz, 1H), 7.44 (t, J = 8.1 Hz, 1H). |

Preparation Example 3

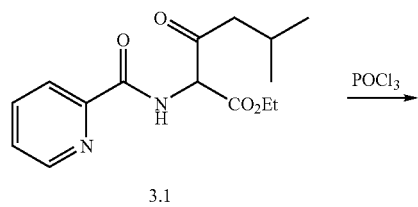

3.1

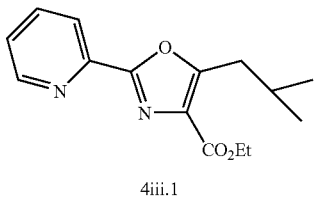

4iii.1

The compound 3.1 (0.6 mmol) and POCl$_3$ (3 mL) were mixed and heated to 80□. The completion degree of the reaction was tracked by TLC. Then the reaction solution was decanted to saturated NaHCO$_3$ solution (50 mL) of 0□, and POCl$_3$ was removed. Then the resulting solution was extracted with ethyl acetate (50 mL), and the solvent was removed completely by concentration. The compound 4iii.1 was obtained by separation through column chromatography with petroleum ether/ethyl acetate (volume ratio 4:1).

Except pyridine-2-carboxylic acid was replaced by the substituted carboxylic acid (compound 1) listed in the following table, the various compounds 3 can be synthesized by the same method as preparation example 1. Then the following target compounds were synthesized by the same method as preparation example 3:

| Compound 4iii | Compound 1 | structure formula of compound 4iii | $^1$H NMR (CDCl$_3$, 300 MHz) data |
|---|---|---|---|
| C274 | pyridine-COOH | pyridine-oxazole(isobutyl)(CO$_2$Et) | δ 0.92 (d, J = 6.6 Hz, 6H), 1.35 (t, J = 7.2 Hz, 3H), 2.13 (m, 1H), 2.96 (d, J = 7.2 Hz, 2H), 4.36 (q, J = 7.2 Hz, 2H), 7.30 (t, J = 5.1 Hz, 1H), 7.73 (t, J = 7.8 Hz, 1H), 8.17 (d, J = 7.8 Hz, 1H), 8.48 (d, J = 4.8 Hz, 1H). |

| Compound 4iii | Compound 1 | structure formula of compound 4iii | ¹H NMR (CDCl₃, 300 MHz) data |
|---|---|---|---|
| C324-4 | quinoline-2-COOH | quinoline-oxazole-CO₂Et with isobutyl | δ 1.01 (d, J = 6.6 Hz, 6H), 1.42 (t, J = 7.2 Hz, 3H), 2.25 (m, 1H), 3.09 (d, J = 7.2 Hz, 2H), 4.43 (d, J = 6.9 Hz, 2H), 7.59 (t, J = 7.2 Hz, 1H), 7.73 (t, J = 7.2 Hz, 1H), 7.77 (d, J = 8.4 Hz, 1H), 8.27 (m, 3H). |

Preparation Example 4

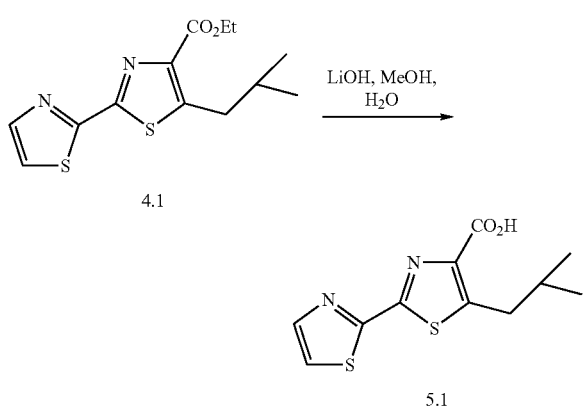

4.1 → 5.1

The compound 4.1 (0.5 mmol) and lithium hydroxide (LiOH) (2 mmol) were mixed, and the mixed solvent of MeOH (4 mL) and water (1 mL) was added. The reaction was conducted at room temperature and tracked by TLC. After the reaction was completed, the solvent was concentrated, and the reaction solution was acidified with 1 mol/L hydrochloric acid (10 mL), extracted with ethyl acetate (25 mL). The solvent was removed completely by concentration to obtain the compound 5.1.

The following compound can be synthesized by the same method.

| compound | structure formula | ¹H NMR (CDCl₃, 300 MHz) data |
|---|---|---|
| Wang268-1 | thiazole-thiazole-COOH with isobutyl | δ 0.11 (d, 6H), 2.03 (m, 1H), 3.33 (d, 2H), 7.40 (d, 1H), 7.80 (d, 1H). |
| Wang268 | thiazole-thiazole-COOH with butyl | δ 0.76 (t, 3H), 1.13 (m, 2H), 1.38 (m, 2H), 2.47 (t, 2H), 7.36 (d, 1H), 7.74 (d, 1H). |
| Wang302 | thiazole-thiazole-COOH with CH₂Ph | δ 4.89 (s, 2H), 7.27 (5H), 7.38 (d, 1H), 7.80 (d, 1H). |

Preparation Example 5

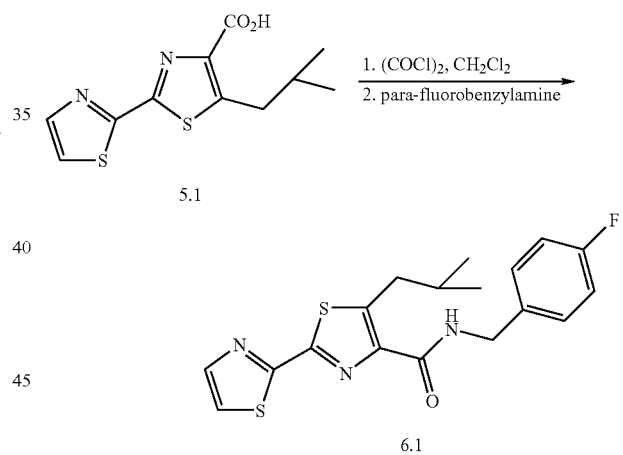

The compound 5.1 (0.5 mmol) was dissolved in dichloromethane (25 mL), and oxalyl Chloride (0.6 mmol) was added. After the resulting mixture was spin dried, ethyl acetate and water (10 mL:10 mL) were added, and sodium bicarbonate (1.0 mmol) was added, then para-fluorobenzylamine (0.6 mmol) was added. After the resulting mixture was agitated at room temperature for several hours, water (10 mL) was added, and extracted with ethyl acetate (25 mL) twice. The organic phase was washed with 1N hydrochloric acid (20 mL) twice and saturated saline one time, and dried over MgSO₄, and then the organic phase was concentrated. The mixture was purified through chromatographic column with petroleum ether/ethyl acetate (volume ratio 4:1) to obtain the product 6.1.

Except para-fluorobenzylamine was replaced by various substituted amine or alcohol listed in the following table, the following compounds were synthesized by the same method as preparation example 5:

| compound | Substituted amine or alcohol | structure formula | ¹H NMR (CDCl₃, 300 MHz) data |
|---|---|---|---|
| W28F | H₂N-CH₂-C₆H₄-F (4-F) | | δ 1.02 (d, J = 6.6 Hz, 6H), 2.03 (m, 1H), 3.31 (d, J = 7.2 Hz, 2H), 4.61 (d, J = 6.0 Hz, 2H), 7.04 (m, 1H), 7.45 (t, J = 8.1 Hz, 2H), 7.35 (m, 2H), 7.44 (d, J = 3.0 Hz, 1H), 7.82 (m, 1H), 7.88 (d, J = 3.0 Hz, 1H). |
| C267 | NH₃ | | δ 1.01 (d, J = 6.6 Hz, 6H), 2.02 (m, 1H), 3.28 (d, J = 6.9 Hz, 2H), 5.60 (bs, 2H), 7.43 (d, J = 3.0 Hz, 1H), 7.88 (d, J = 3.0 Hz, 1H). |
| C357 | H₂N-CH₂-Ph | | δ 1.02 (d, J = 6.6 Hz, 6H), 2.04 (m, 1H), 3.31 (d, J = 7.2 Hz, 2H), 4.64 (d, J = 6.3 Hz, 2H), 7.34 (bm, 5H), 7.85 (d, J = 3.3 Hz, 2H). |
| C343 | H₂N-Ph | | δ 1.02 (d, J = 6.6 Hz, 6H), 2.04 (m, 1H), 3.31 (d, J = 7.2 Hz, 2H), 4.64 (d, J = 6.3 Hz, 2H), 7.34 (bm, 4H), 7.85 (d, J = 3.3 Hz, 1H). |
| C295-3 | HN(Me)₂ | | δ 0.93 (d, J = 6.6 Hz, 6H), 1.90 (m, 1H), 2.84 (d, J = 6.9 Hz, 2H), 3.02 (s, 3H), 3.09 (s, 3H), 7.39 (d, J = 3.3 Hz, 1H), 7.82 (d, J = 3.0 Hz, 1H). |
| C281 | MeNH₂ | | δ 0.98 (d, J = 6.6 Hz, 6H), 1.99 (m, 1H), 2.98 (d, J = 4.8 Hz, 3H), 3.26 (d, J = 7.2 Hz, 2H), 7.42 (d, J = 3.3 Hz, 1H), 7.44 (bs, 1h), 7.85 (d, J = 3.3 Hz, 1H). |
| C310-4 (W28D) | iPrOH | | δ 1.00 (d, 6H), 1.42 (d, 6H), 2.00 (m, 1H), 3.12 (d, 3H), 5.29 (m, 1H), 7.45 (d, 1H), 7.86 (d, 1H). |
| C324-6 | tBuOH | | δ 0.93 (d, J = 6.6 Hz, 6H), 1.64 (s, 9H), 1.93 (m, 1H), 3.04 (d, J = 7.5 Hz, 2H), 7.40 (d, J = 3.0 Hz, 1H), 7.80 (d, J = 3.0 Hz, 1H). |

-continued

| compound | Substituted amine or alcohol | structure formula | ¹H NMR (CDCl₃, 300 MHz) data |
|---|---|---|---|
| C503 | | | δ 1.01 (m, 12H), 1.93 (m, 1H), 2.05 (m, 1H), 2.81 (d, J = 6.9 Hz, 2H), 3.31 (d, J = 7.2 Hz, 2H), 4.70 (d, J = 4.2 Hz, 2H), 7.04 (m, 1H), 7.44 (d, J = 3.0 Hz, 2H), 7.88 (d, J = 3.0 Hz, 2H), 8.18 (bs, 1H). |
| W28MF | | | δ 1.01 (d, J = 6.3 Hz, 6H), 2.01 (m, 1H), 2.52 (s, 3H), 3.29 (d, J = 6.9 Hz, 2H), 4.60 (d, J = 5.4 Hz, 2H), 7.05 (d, J = 8.1 Hz, 2H), 7.34 (m, 2H), 7.52 (s, 1H), 7.78 (bs, 1H). |

Preparation Example 6

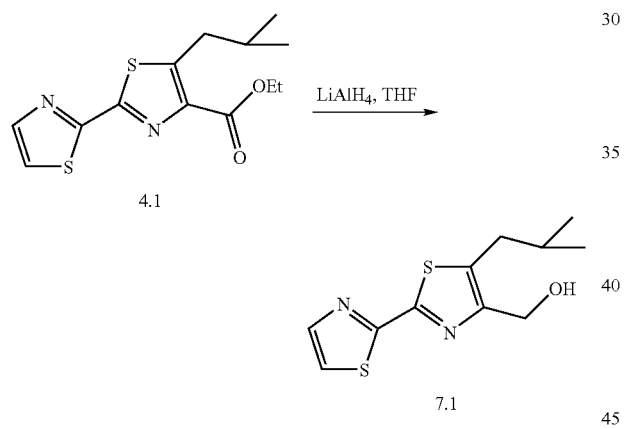

The compound 4.1 (0.5 mmol) was dissolved in anhydrous THF (25 mL), and aluminum lithium hydride (LiAlH₄) (0.6 mmol) was added. The reaction was conducted in ice bath and tracked by TLC. After the reaction was completed, the reaction solution was diluted with water (25 mL), and extracted with ethyl acetate (25 mL). The solvent was removed completely by concentration. The compound 7.1 was obtained by separation through chromatographic column with petroleum ether/ethyl acetate (volume ratio 4:1).

| compound | structure formula | ¹H NMR (CDCl₃, 300 MHz) data |
|---|---|---|
| C254 | | δ 0.96 (d, J = 6.6 Hz, 6H), 1.88 (m, 1H), 2.71 (d, J = 7.2 Hz, 2H), 2.91 (bs, 1H), 4.70 (s, 2H), 7.38 (d, J = 3.0 Hz, 1H), 7.83 (d, J = 3.3 Hz, 1H). |

Preparation Example 7

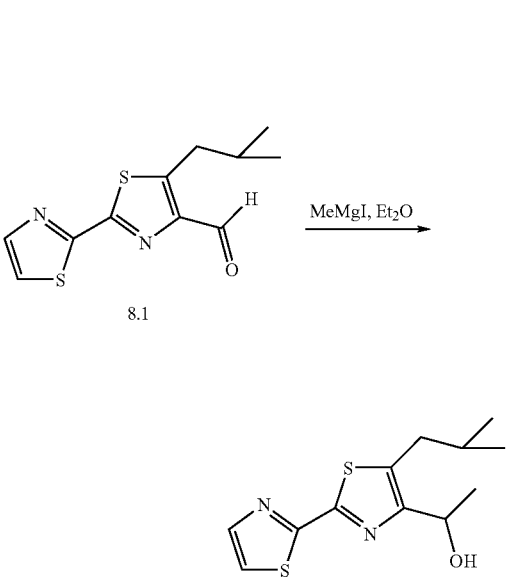

The compound 7.1 (1 mmol) and IBX (1.25 mmol) were mixed, and the mixed solvent of toluene and DMSO (2 mL:1 mL) was added. The reaction was conducted at 50□ and tracked by TLC. After the reaction was completed, the reaction solution was extracted with ethyl acetate (25 mL), and the solvent was removed completely to obtain the compound 8.1. The compound 8.1 was dissolved in absolute ether (10 mL), and methyl Grignard reagent (1.2 mmol) was added dropwise. The reaction was conducted at room temperature and tracked by TLC. After the reaction was completed, the reaction solution was diluted with water (25 mL), and extracted with ethyl acetate (25 mL), then the solvent was removed completely by concentration. The compound 9.1 was obtained by separation through chromatographic column with petroleum ether/ethyl acetate (volume ratio 2:1).

Except methyl Grignard reagent was replaced by ethyl Grignard reagent, the following compound C282-2 was synthesized by the same method as preparation example 7:

| compound | structure formula | $^1$H NMR (CDCl$_3$, 300 MHz) data |
|---|---|---|
| C268-2 | | δ 0.96 (d, J = 6.6 Hz, 6H), 1.57 (d, J = 6.6 Hz, 3H), 1.90 (m, 1H), 2.70 (d, J = 7.2 Hz, 2H), 3.07 (bs, 1H), 4.95 (m, 1H), 7.39 (d, J = 3.0 Hz, 1H), 7.84 (d, J = 3.0 Hz, 1H), H). |
| C282-2 | | δ 0.96 (m, 9H), 1.90 (d, J = 6.6 Hz, 3H), 2.68 (d, J = 7.2 Hz, 2H), 4.64 (m, 1H), 7.38 (d, J = 3.3 Hz, 1H), 7.82 (d, J = 3.0 Hz, 1H). |

Preparation Example 8

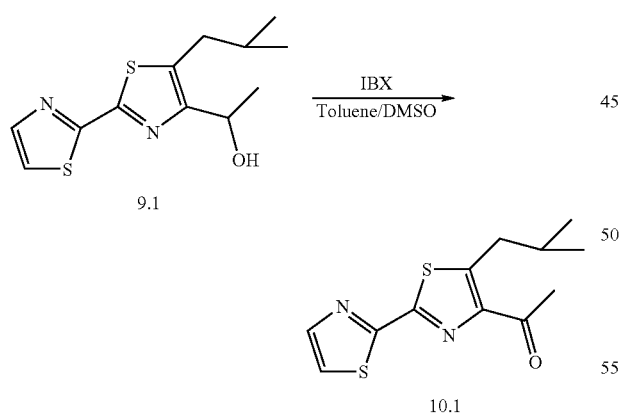

The compound 9.1 (0.5 mmol) and IBX (0.6 mmol) were mixed, and the mixed solvent of toluene and DMSO (2 mL:1 mL) was added. The reaction was conducted at 50□ and tracked by TLC. After the reaction was completed, the reaction solution was diluted with water (25 mL), and extracted with ethyl acetate (25 mL), and then the solvent was removed completely by concentration to obtain the compound 10.1. The following compound C280-4 can be synthesized from compound C282-2 by the same method:

| compound | structure formula | $^1$H NMR (CDCl$_3$, 300 MHz) data |
|---|---|---|
| C266 | | δ 0.99 (d, J = 6.6 Hz, 6H), 1.99 (m, 1H), 2.71 (s, 3H), 3.17 (d, J = 6.9 Hz, 2H), 7.45 (d, J = 3.3 Hz, 1H), 7.89 (d, J = 3.0 Hz, 1H). |
| C280-4 | | δ 0.98 d, J = 6.6 Hz, 6H), 1.20 (t, J = 7.2 Hz, 2H), 1.99 (m, 1H), 3.17 (m, 4H), 7.44 (d, J = 3.3 Hz, 1H), 7.86 (d, J = 3.0 Hz, 1H). |

Preparation Example 9

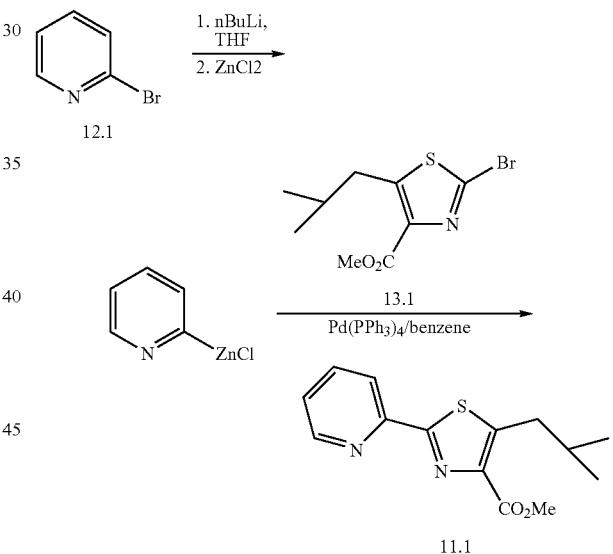

The compound 12.1 (1.0 mmol) was dissolved in anhydrous THF, and nBuLi (1.05 mmol) was added dropwise at −78□. After the reaction was conducted for half an hour, anhydrous zinc chloride (1.1 mmol) was added. After the reaction solution was agitated for half an hour at room temperature, the compound 13.1 (11.0 mmol) and catalyst (0.05 mmol) were added, and the benzene as solvent (10 mL) was added and reacted for 12 hours at 80□. The reaction was tracked by TLC. After the reaction was completed, the solvent was removed completely by concentration. The product was diluted with water (25 mL), and extracted with ethyl acetate (25 mL). Then the solvent was removed completely by concentration. The compound 11.1 was obtained by separation through chromatographic column with petroleum ether/ethyl acetate (volume ratio 4:1).

| compound | structure formula | $^1$H NMR (CDCl$_3$, 300 MHz) data |
|---|---|---|
| C276 | 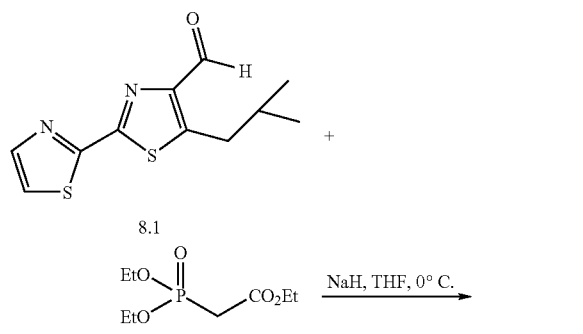 | δ 0.98 (d, J = 6.6 Hz, 6H), 2.00 (m, 1H), 3.16 (d, J = 7.2 Hz, 2H), 3.94 (s, 3H), 7.32 (t, J = 5.1 Hz, 1H), 779 (t, J = 1.8 Hz, 1H), 8.27 (d, J = 7.5 Hz, 1H), 8.58 (d, J = 4.2 Hz, 1H). |
| C322-2 | | δ 0.99 (d, J = 6.6 Hz, 6H), 1.35 (t, J = 7.2 Hz, 3H), 1.95 (m, 1H), 2.84 (d, J = 7.5 Hz, 2H), 4.29 (q, J = 7.2 Hz, 2H), 6.90 (d, J = 15.3 Hz, 1H), 7.44 (d, J = 3.0 Hz, 1H), 7.63 (d, J = 15.3 Hz, 1H), 7.88 (d, J = 3.0 Hz, 1H). |
| C324-5 | | δ 0.95 (d, J = 6.6 Hz, 6H), 1.23 (t, J = 7.2 Hz, 3H), 1.87 (m, 1H), 2.67 (d, J = 7.2 Hz, 3H), 2.76 (t, J = 7.2 Hz, 2H), 2.98 (t, J = 7.2 Hz, 2H), 4.13 (q, J = 7.2 Hz, 2H), 7.34 (d, J = 3.0 Hz, 1H), 7.81 (d, J = 3.0 Hz, 1H). |

Preparation Example 10

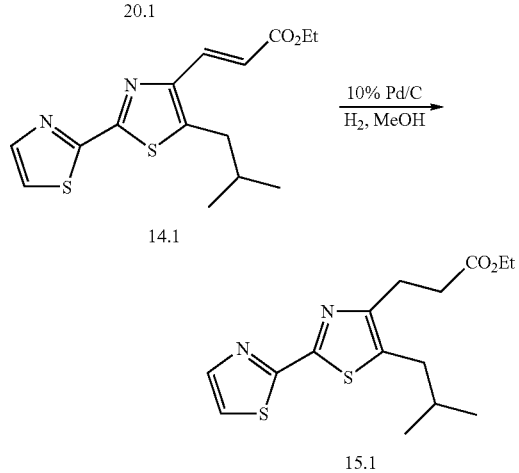

Preparation Example 11

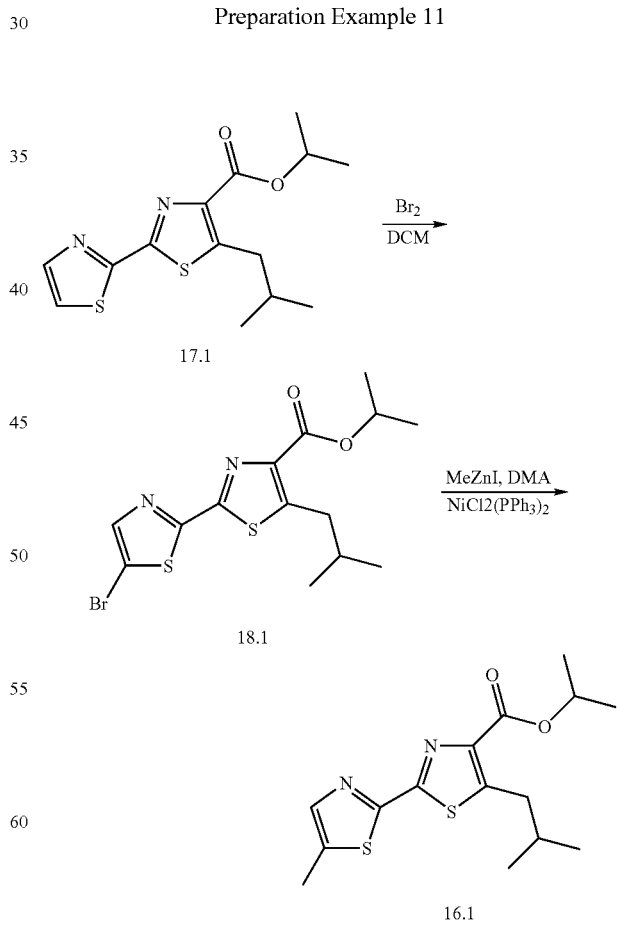

The compound 20.1 (1.05 mmol) was dissolved in anhydrous THF (10 mL), and NaH (1.05 mmol) was added at 0□. After the reaction was conducted for half an hour, the compound 8.1 (1.0 mmol) was added and reacted for 12 hours at 0□ under stirring. The reaction was tracked by TLC. After the reaction was completed, the solvent was removed completely by concentration. The product was diluted with water (25 mL) and extracted with ethyl acetate (25 mL). Then the solvent was removed completely by concentration. The compound 14.1 was obtained by separation through chromatographic column with petroleum ether/ethyl acetate (volume ratio 4:1). The compound 14.1 was dissolved in MeOH (10 mL) with adding 10% Pd/C and hydrogenated at room temperature overnight. The compound 15.1 was obtained by vacuum filtration.

The compound 17.1 (1.0 mmol) was dissolved in DCM (10 mL) with adding liquid bromine (1.2 mmol). The reaction was conducted for 12 hours at room temperature and tracked by TLC. After the reaction was completed, the solvent was removed completely by concentration. The remainder was extracted with ethyl acetate (25 mL), and the compound 18.1 was obtained by separation through chromatographic column with petroleum ether/ethyl acetate (volume ratio 4:1). The iodomethane (1.2 mmol) and active zinc powder (1.3 mmol) were reacted in DMA to obtain zincon (1.2 mmol), then compound 18.1 and catalyst (10%) were added. After the reaction was conducted for 3 hours at room temperature, the reaction solution was diluted with water (25 mL) and extracted with ethyl acetate (25 mL). Then the solvent was removed completely by concentration to obtain the crude product. The crude product was separated through chromatographic column with petroleum ether/ethyl acetate (volume ratio 4:1) to obtain the compound 16.1.

| compound | structure formula | $^1$H NMR (CDCl$_3$, 300 MHz) data |
|---|---|---|
| W28M | 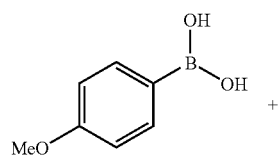 | δ 0.97 (d, J = 6.6 Hz, 6H), 1.39 (d, J = 6.3 Hz, 6H), 1.95 (m, 1H), 2.50 (s, 3H), 3.09 (d, J = 7.2 Hz, 2H), 5.26 (m, 1H), 7.50 (s, 1H). |

Preparation Example 12

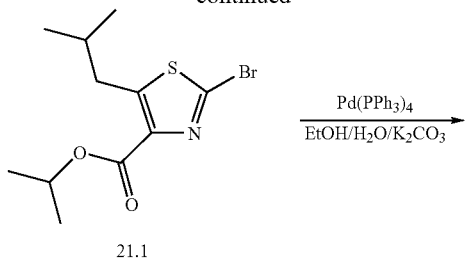

21.1

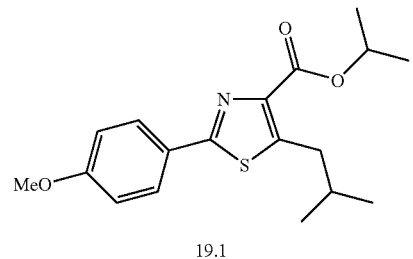

19.1

The para-methoxybenzeneboronic acid reagent (1.0 mmol) was dissolved in ethanol (10 mL), then adding water (2 mL), potassium carbonate (3.0 mmol), compound 21.1 (1.0 mmol) and the catalyst (0.05 mmol). The reaction was conducted for 12 hours at 80□ and tracked by TLC. After the reaction was completed, the solvent was removed completely by concentration. The remainder was diluted with water (25 mL), and extracted with ethyl acetate (25 mL). The solvent was removed completely by concentration, and the compound 19.1 was obtained by separation through chromatographic column with petroleum ether/ethyl acetate (volume ratio 5:1).

| compound | structure formula | $^1$H NMR (CDCl$_3$, 300 MHz) data |
|---|---|---|
| C37 | | δ 0.99 (d, J = 5.4 Hz, 6H), 1.41 (d, J = 6.0 Hz, 6H), 1.98 (m, 1H), 3.09 (d, J = 7.2 Hz, 2H), 3.85 (s, 3H), 5.28 (m, 1H), 6.93 (d, J = 8.7 Hz, 2H), 7.89 (d, J = 9.0 Hz, 2H). |

Preparation Example 13

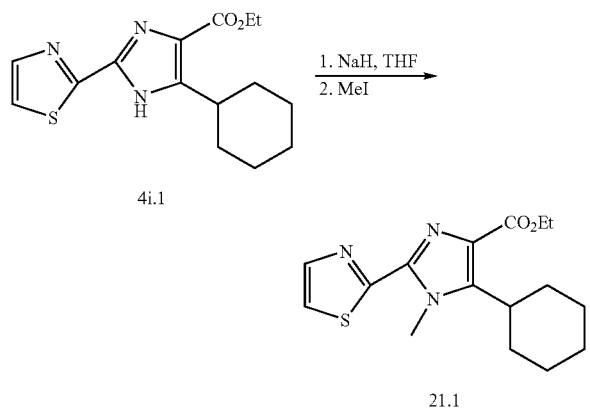

The compound 4i.1 (1.0 mmol) was dissolved in anhydrous tetrahydrofuran (10 mL), and NaH (1.2 mmol) was added. After the reaction was conducted for 1 hour at room temperature, iodomethane (3.0 mmol) was added, after that the reaction further was conducted for 12 hours at room temperature. The reaction was tracked by TLC. After the reaction was completed, the reaction solution was concentrated to remove the solvent completely, and acidified with 5% hydrochloric acid, diluted with water (20 mL), then extracted with ethyl acetate (25 mL). The solvent was removed completely by concentration, and the compound 21.1 was obtained by separation through chromatographic column with petroleum ether/ethyl acetate (volume ratio 5:1).

| compound | structure formula | $^1$H NMR (CDCl$_3$, 300 MHz) data |
|---|---|---|
| C319-6 | 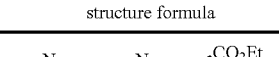 | δ 1.48 (m, 5H), 1.73 (m, 4H), 1.83 (m, 4H), 3.20 (m, 1H), 4.35 (s, 3H), 4.37 (q, 2H), 7.39 (d, 1H), 7.89 (d, 1H). |

Experimental Example

Experimental Example 1

Experiment of Anti Hepatitis B Virus (HBV) Activity Test

1. Object of the Experiment:

The sample compounds are screened for their anti hepatitis B virus (HBV) activity. The experiment includes: testing the effect of cytotoxicity of the sample compounds on secretion of the surface antigen and core antigen of hepatitis B virus and on replication of virus nucleic acid (DNA) through the virus-cell level experiment.

2. Principle of the Experiment:

Hepatitis B virus (HBV) transgenic human hepatoma carcinoma cell, HepG2.2.15 cell line, can secrete hepatitis B virus particles (containing antigen and DNA) into the supernatant when being incubated.

Under the influence of antiviral drugs, the contents of HBsAg, HBeAg and viral DNA secreted from cells into the supernatant were detected. Compared with the contents of control groups without drugs, the antiviral activity of the sample drugs can be observed. Meanwhile, the cytotoxic effect of the sample drugs can be detected. The value concentration of the sample drugs which caused 50% of the cells dead measured with MTT method was $CC_{50}$. And the value concentration of the sample drugs which inhibited 50% of the secretion of HBsAg and HBeAg detected by specific ELISA kits and inhibited 50% of the viral DNA replication detected by fluorescent quantitation PCR method was $IC_{50}$.

3. Samples of the Experiment:

The solutions of the sample drugs having required concentration (1 mM) were prepared before use. Each sample drug was tested with 7 dilution concentrations, and the antiviral drugs such as Lamivudine etc. were used as the positive control drugs to check whether each experiment was normal or not each time.

4. Method of the Experiment:

a) Experimental Process and Collection of Supernatant

HepG2.2.15 cells were inoculated into a 96-well plate, and the sample drugs were added next day. The medium and the sample drugs with the same concentration were renewed periodically, and the supernatants were collected on the eighth day to be detected. MTT was added to the cells in the 96-well plate, and MTT dissolving solution was added after 4 hours and reacted overnight. $OD_{570}$ was measured on ELISA the next day. The cytotoxicity of the sample drugs to HepG2.2.15 cells, the effect of the sample drugs on the growth of the cells, and the concentration of the sample drugs ($CC_{50}$) resulting in 50% of the cells dead were estimated according to the OD values.

b) Detection of the Contents of HBsAg and HBeAg in Supernatant (ELISA Method):

HBsAg and HBeAg were detected with reagent kits (Purchased from Sin θ-American Biotechnological Company). The samples were added to the coated strip plate, and the same amount of enzyme labeled conjugate was added. After reacted for one hour at 37□, the plate was washed 5 times. The colorant Solutions A and B were added, and the reaction was stopped after 15 minutes, and $OD_{450/630}$ was measured. The half inhibition concentration ($IC_{50}$) of the sample for the HBV antigen was estimated according to the OD values.

c) Detection of the Content of HBV-DNA in Supernatant by Fluorescent Quantification PCR:

A suitable amount of supernatant was added to the same volume of virus extract solution, and was boiled after mixed homogenously, then centrifuged at 10000 rpm under room temperature for 5 minutes, and a suitable amount of supernatant was collected for PCR amplification. Meanwhile five HBV-DNA standard samples were set to establish a standard curve. According to the obtained viral DNA replication value, the inhibition ratios of HBV-DNA replication of each sample drug at different concentrations were calculated, and then the half inhibition rates of the sample drugs were calculated to obtain $IC_{50}$. For those samples that can not be calculated for $IC_{50}$ values, they can be represented by ICx and list the corresponding concentration values.

The PCR primers used in the experiment were:

```
P1: 5'ATCCTGCTGCTATGCCTCATCTT3'

P2: 5' ACAGTGGGGAAAGCCCTACGAA3'.
```

The PCR probe used in the experiment was:

5'TGGCTAGTTTACTAGTGCCATTTTG3'

5. Experimental Results:

| Sample No. | Cytotoxicity $CC_{50}$ (μM) | HbsAg secretion $IC_{50}$ (SI) (μM) | HBeAg secretion $IC_{50}$ (SI) (μM) | DNA replication $IC_{50}/IC_X$ (SI) (μM) |
|---|---|---|---|---|
| C290 | >100 | NT | NT | 0.14 (>714) |
| C290-3 | >100 | NT | NT | NA |
| C306-2 | >100 | NT | NT | 0.14 (>714) |
| C306-3 | 5.67 | NT | NT | 0.14 (>40.5) |
| C290-2 | >100 | NT | NT | NA |
| C274 | >100 | NT | NT | 67.6 (>1.5) |
| C323-2 | >100 | NT | NT | NA |
| C324-4 | 45.4 | NT | NT | 11.9 (4) |
| C375 | >33.3 | NT | NT | >33.3 |
| C307-2 | >33.3 | NT | NT | NA |
| C307-3 | >33.3 | NT | NT | <0.05 (>666) |
| C307-4 | >33.3 | NT | NT | 0.14 (>237.9) |
| C319-3 | >33.3 | NT | NT | 0.09 (>370) |
| C319-4 | >33.3 | NT | NT | 0.11 (>302.7) |
| C319-5 | >33.3 | NT | NT | 0.04 (>832.5) |
| C334-2 | >33.3 | NT | NT | 1.06 (>31.4) |
| C334-3 | >33.3 | NT | NT | 1.2 (>27.75) |
| C334-4 | >33.3 | NT | NT | 1.24 (>26.9) |
| C404 | >33.3 | NT | NT | NA |
| C323-3 | >33.3 | NT | NT | NA |
| C254 | >33.3 | NT | NT | >33.3 |
| C358 | >33.3 | NT | NT | IC36 = 1.23 |
| C303-1 | >33.3 | NT | NT | 2.9 (>11.5) |
| C303-2 | >33.3 | NT | NT | >33.3 |
| C303-3 | >33.3 | NT | NT | 1.48 (>22.5) |
| C296-4 | >33.3 | NT | NT | 0.2 (>166.5) |
| C364-1 | 19.2 | NT | NT | 1.1 (18) |
| C364-2 | >33.3 | NT | NT | NA |
| C305-4 | >33.3 | NT | NT | NA |
| C268-1 | >33.3 | NT | NT | 1.3 (>25.6) |
| C282-1 | >33.3 | NT | NT | <0.05 (>666) |
| C268-2 | >33.3 | NT | NT | 0.6 (>55.5) |
| C282-2 | >33.3 | NT | NT | 0.8 (>41.6) |
| C266 | >33.3 | NT | NT | 0.06 (>555) |
| C280-4 | >33.3 | NT | NT | 0.09 (>370) |
| C322-2 | >33.3 | NT | NT | 0.06 (>555) |
| C324-5 | >33.3 | NT | NT | 3 (>11.1) |
| C324-6 | >33.3 | NT | NT | 3.7 (>9) |
| C310-4 (W28D) | >100 | NT | NT | 0.81 (>123) |
| W28F | 43 | NT | NT | 0.78 (55) |
| W28M | >20 | NT | NT | <0.08 (>250) |
| W28 | >333 | 67.57 (>4.93) | 21.67 (>15.4) | 2.4 (>138.8) |
| C37 | >33 | NT | NT | 0.03 (>1100) |
| Wang268 | 256.7 | 37.2 (6.9) | 127.7 (2) | IC53 = 125 |
| Wang302 | 192.2 | NC | 83.2 (2.3) | 63.1 (3.1) |
| C295-3 | >100 | NT | NT | IC12 = 1.23 |
| C281 | >100 | NT | NT | IC94 = 33 |
| C343 | 50 | NT | NT | IC19 = 1.23 |
| C267 | >100 | NT | NT | IC89 = 33 |

Note:
$CC_{50}$ indicates the effect of the sample drugs on the growth of HepG2.2.15 cells, 50% death concentration.
$IC_{50}$ is the concentration of sample drugs that inhibits 50% of the antigen or DNA replication.
SI is the selection index of the bioactivity of the samples. SI value >2 means effective and the greater SI value is better.
NA means no obvious biological activity or unable to be calculated. NT means no test. NC means no results.

It can be seen from the experiment results that most of this kind of compounds have inhibition activity to HBV DNA replication on cellular level, wherein $IC_{50}$ values of 19 compounds were less than 1 μM, and $IC_{50}$ values of 8 compounds were less than 0.1 μM.

Experimental Example 2

Experiment of Anti Hepatitis B Virus (HBV) Activity Test on Animal

1. Drugs

The solutions of the sample drugs having required concentration (100 mg/mL) were prepared by using 0.3% sodium carboxymethyl cellulose. Batch number: 00701010

Positive drug, Lamivudine, a product of Glaxo Wellcome pharmaceutical Co., was prepared with normal saline. Batch number: 005110011

2. Virus:

Strong positive serum of Duck hepatitis B virus DNA (DHBV-DNA), collected from Shanghai brown-duck, was store at −70□.

3. Animals:

1-day-old Beijing duck, purchased from Beijing QianJin breeding duck farm.

4. Reagents

α-$^{32}$P-dCTP was purchased from Beijing FuRui Biotechnology Co. Nick translation kit was purchased from Promega Co.; Sephadex G-50, Ficoll PVP was purchased from Pharmacia Co. (Sweden); SDS was purchased from Merck Co. (Germany); fish sperm DNA, Bovine serum albumin were products of Biophysics Institute of Chinese Academy of Science; Nitrocellulose membrane (0.45 nm) was product of Amersham Co.

5. Method:

a). Duck Hepatitis B Virus Infection:

1-day-old Beijing duck was injected DHBV-DNA positive serum of Shanghai brown-duck via vena cruralis with 0.2 ml/each duck. Blood was taken on the seventh day after infected; serum was separated and stored at −70□ to be detected.

b). Drug Treatment Experiment:

DHBV infected ducklings were randomly grouped (six ducklings/each group) to carry out drug treatment experiment after 7 days. The administration groups (W28D, W28F, W28M, C37) were set 1 dose group—50 mg/kg respectively, and oral (intragastric) administered twice per day for 10 days (Bid×10). The drugs were replaced with normal saline in virus control group (DHBV). The positive drug was Lamivudine, which was oral (intragastric) administrated with 50 mg/kg, twice per day for 10 days. Blood was taken from the vena cruralis of the duck after 7 days later of infection, i.e. before drug administration (T0), the fifth day (T5) and the tenth day after drug administration (T10), and the third day after drug withdrawal (P3), then serum was separated and stored at −70□ to be detected.

c). Detection Method:

The above duck serum was taken and dotted on the membrane to measure the dynamic level of DHBV-DNA in the duck serum. According to the instruction of nick translation kit, dot blot hybridization of duck serum and was carried out using $^{32}$P labeled DHBV-DNA probe (purchased from Promega Co.). And the dots were shown on the membrane by radioautography. The OD values (the filter was 490 nm) of the dots on the membrane were measured by ELISA. DHBV-DNA density of the serum was calculated and the OD values of the hybridized dot were used as the values of DHBV-DNA level.

6. Calculation of Drug Action:

a) The mean values (X±SD) of DHBV-DNA OD values of serum at different time of the ducks in each group were calculated, and the DNA levels of serum at different time after drug administration (T5, T10) and the third day after drug withdrawal (P3) for the ducks in each group and were compared with the OD values before administration (T0) of the same group. The values of t1 and P1 were calculated by paired-t test. The significance of the difference was analyzed, and the inhibitory effect of the drugs on the viral infection was estimated.

b). The inhibition ratio (%) to DHBV-DNA of serum at different time after administration (T5, T10) and the third day after drug withdrawal (P3) of the ducks in each group were calculated and illuminated in the figure, and the dynamic state of the inhibition ratios of DHBV-DNA in duck serum in each group were compared.

$$DNA\ inhibition\ \% = \frac{OD\ \text{value before administration}\ (T0) - OD\ \text{value after administration}\ (T5, T10, P3)}{OD\ \text{Value before administration}\ (T0)} \times 100$$

c) The inhibitions % of DHBV-DNA at different time of the administration group were compared with that at the same time of the virus control group. The result was statistically treated with group t test, and the values of t2 and P2 were calculated. The significance of the difference was analyzed, and the drug action was estimated.

7. Experimental Results:

FIG. 1 is the comparison of the inhibition ratio of DHBV-DNA level in duck serum of the treating group and that of the control group with virus infection, after the ducks infected by the duck hepatitis B virus were orally (intragastric) administered.

With regard to 4 group with administrating drugs of the 50 mg/kg, after the ducks were orally (intragastric) administered twice per day for 10 days, no change of the common condition and food intake of the ducks were observed.

In both paired and group analysis, the positive control drug, Lamivudine, of 50 mg/kg group showed inhibitory effect to DHBV-DNA, which means the experiment was tenable. 3 days after withdrawal of the drugs, DHBV-DNA rebounded to the original level.

At the condition of the present experiment, for W28F 50 mg/kg, both paired analysis and group analysis of T5 and T10 showed inhibitory effect to DHBV-DNA with statistical significance. Though DHBV-DNA at P3 rebounded, it did not reach the original level. For W28M 50 mg/kg group, though paired analysis of T10 and P3 showed inhibitory effect to DHBV-DNA with statistical significance, the group analysis did not show any effect with statistical significance. For W28D 50 mg/kg group, both paired analysis and group analysis T10 showed inhibitory effect to DHBV-DNA with statistical significance. For C37 50 mg/kg group, the paired analysis and group analysis at each time point did not show inhibitory effect to DHBV-DNA.

The invention claimed is:

1. A heterocyclic non-nucleoside compound represented by the following structure formula:

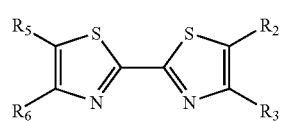

wherein each $R_5$ and $R_6$ independently is hydrogen atom, halogen atom, or phenyl;

$R_2$ is linear or branched $C_1$-$C_8$ alkyl, $C_3$-$C_8$ cycloalkyl or benzyl;

$R_3$ is one selected from the group consisting of $C_1$-$C_6$ hydroxyalkyl; $C_1$-$C_4$ alkyl substituted by $C_1$-$C_4$ alkoxycarbonyl; $C_2$-$C_4$ alkenyl substituted by $C_1$-$C_4$ alkoxycarbonyl;

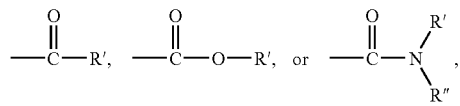

wherein each R' and R" independently is selected from the group consisting of halogenated $C_1$-$C_{10}$ alkyl, halogenated benzyl, benzyl substituted by $C_1$-$C_{10}$ alkyl, benzyl substituted by $C_1$-$C_{10}$ alkoxyl, benzyl substituted by $C_1$-$C_{10}$ alkylamino group, benzyl substituted by nitrile group, benzyl substituted by carboxyl, and benzyl substituted by $C_1$-$C_{10}$ alkyloxycarbonyl.

2. The heterocyclic non-nucleoside compound according to claim 1, wherein said heterocyclic non-nucleoside compounds are one of the following compounds:

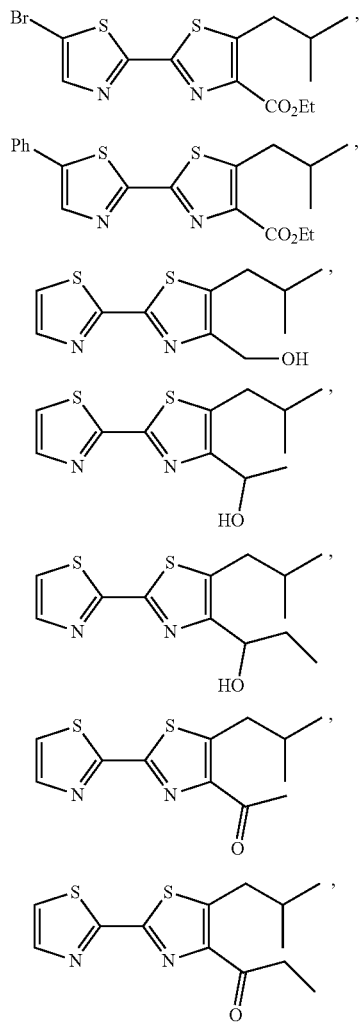

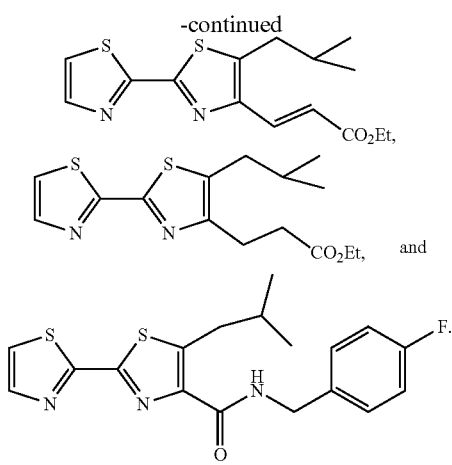

3. An antiviral pharmaceutical composition consisting of the heterocyclic non-nucleoside compound according to claim 1 as an active component and a pharmaceutically common adjuvant.

4. A heterocyclic non-nucleoside compound selected from the following structure formula:

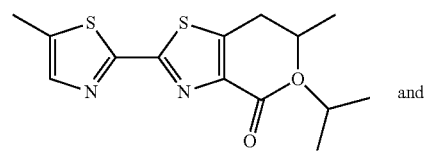

and

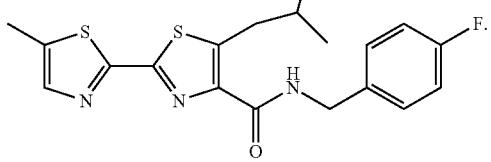

5. An antiviral pharmaceutical composition consisting of the heterocyclic non-nucleoside compound according to claim 4 as an active component and a pharmaceutically common adjuvant.

\* \* \* \* \*